(12) United States Patent
Rietman et al.

(10) Patent No.: US 11,515,004 B2
(45) Date of Patent: Nov. 29, 2022

(54) THERMODYNAMIC MEASURES ON PROTEIN-PROTEIN INTERACTION NETWORKS FOR CANCER THERAPY

(71) Applicant: CSTS HEALTH CARE INC., Toronto (CA)

(72) Inventors: Edward A. Rietman, Nashua, NH (US); Giannoula Lakka Klement, Boston, MA (US)

(73) Assignee: CSTS HEALTH CARE INC.

(*) Notice: Subject to any disclaimer, the term of this patent is extended or adjusted under 35 U.S.C. 154(b) by 980 days.

(21) Appl. No.: 15/576,520

(22) PCT Filed: May 20, 2016

(86) PCT No.: PCT/CA2016/050581
§ 371 (c)(1),
(2) Date: Apr. 20, 2018

(87) PCT Pub. No.: WO2016/187708
PCT Pub. Date: Dec. 1, 2016

(65) Prior Publication Data
US 2018/0260519 A1  Sep. 13, 2018

Related U.S. Application Data

(60) Provisional application No. 62/165,879, filed on May 22, 2015.

(51) Int. Cl.
*G16B 20/20* (2019.01)
*G16B 20/00* (2019.01)
(Continued)

(52) U.S. Cl.
CPC .............. *G16B 20/20* (2019.02); *G06F 17/11* (2013.01); *G16B 5/00* (2019.02); *G16B 20/00* (2019.02); *G16B 45/00* (2019.02)

(58) Field of Classification Search
CPC .......... G06T 7/0014; G06T 7/12; G06T 7/00; G06T 2207/20081; G06T 7/60;
(Continued)

(56) References Cited

U.S. PATENT DOCUMENTS

| | | | |
|---|---|---|---|
| 7,213,009 B2 | 5/2007 | Pestotnik et al. | |
| 7,991,221 B1 * | 8/2011 | Kling | G06K 9/6252 |
| | | | 382/154 |

(Continued)

FOREIGN PATENT DOCUMENTS

| | | |
|---|---|---|
| CA | 2899264 A1 | 8/2014 |
| WO | 03017038 A2 | 2/2003 |

(Continued)

OTHER PUBLICATIONS

Singh, R. et al. Struct2Net: a web service to predict protein-protein interactions using a structure based approach. (2010) Nucleic acids research, vol. 38, W509. (Year: 2010).*

(Continued)

*Primary Examiner* — Mary K Zeman
(74) *Attorney, Agent, or Firm* — Ferguson Braswell Fraser Kubasta PC

(57) ABSTRACT

A method to select a protein target for therapeutic application includes accessing genomic information and protein-protein interaction (PPI) data, computing a thermodynamic measure for each protein node within the network of protein nodes, generating an energy landscape data corresponding to the network of protein nodes and the thermodynamic measure, generating a PPI subnetwork by applying a topological filtration to the energy landscape data of the PPI data, computing a first Betti number for the PPI subnetwork, sequentially removing a protein node(s) from the PPI subnetwork while replacing the previously removed node(s), computing a new Betti number for the PPI subnetwork with (Continued)

the protein node(s) removed, computing a change between the Betti numbers, and determining, based on the change between the Beti numbers, a most significant protein target within the PPI subnetwork.

12 Claims, 14 Drawing Sheets

(51) Int. Cl.
  *G16B 5/00* (2019.01)
  *G16B 45/00* (2019.01)
  *G06F 17/11* (2006.01)
(58) Field of Classification Search
  CPC ......... G06T 2207/20084; G06T 11/006; G06T 19/003; G06T 7/13; G06N 20/00; G06N 3/08; G06N 3/0454; G06N 3/0445; G06N 20/10; G06N 3/04; G06N 7/005; G06N 3/0418; G06N 3/082; G06N 5/04; G06N 3/0472; G06N 3/084; G06N 3/088; G06K 9/00147; G06K 9/00536; G06K 9/00523; G06K 9/6267; G06K 9/6232; G06K 9/6256; G06K 9/6268; G06K 9/52; G06K 9/469; G06K 9/50; G16B 20/00; G16B 45/00; G16B 5/00; G16B 30/00; G16B 5/20; G16B 10/00; G16B 15/20; G16B 15/30; G16B 20/30; G16B 40/20; G16B 15/00; G06F 17/11; G06F 17/16; G06F 2111/10; G06F 30/20; G06F 17/18; G06F 16/285; G06F 17/14; G06F 17/142; G06F 16/24578; G16H 50/20; G16H 10/60; G16H 50/50; G16H 50/70; G16H 15/00; G16H 30/20; C12Q 1/6827; C12Q 2600/106; C12Q 2600/156; C12Q 2600/158
  See application file for complete search history.

(56) References Cited

U.S. PATENT DOCUMENTS

| | | | |
|---|---|---|---|
| 8,000,948 | B2 | 8/2011 | Bugrim et al. |
| 8,489,334 | B2 | 7/2013 | Chen et al. |
| 8,718,377 | B2 * | 5/2014 | Suzuki ............... G06T 7/0012 382/192 |
| 9,430,688 | B1 * | 8/2016 | Ray ........................ G06K 9/38 |
| 10,475,183 | B2 * | 11/2019 | Kawaguchi ............ G01N 21/84 |
| 2006/0008831 | A1 | 1/2006 | Sreekumar |
| 2006/0194949 | A1 | 8/2006 | Downes |
| 2006/0235670 | A1 | 10/2006 | Vujasinovic |
| 2007/0036434 | A1 * | 2/2007 | Saveliev ................. G06K 9/52 382/173 |
| 2007/0038385 | A1 | 2/2007 | Nikolskaya |
| 2007/0134662 | A1 * | 6/2007 | Singh .................... G16B 15/00 435/6.14 |
| 2009/0304805 | A1 | 12/2009 | Desai |
| 2011/0064732 | A1 | 3/2011 | De Haas |
| 2011/0217297 | A1 | 9/2011 | Kao |
| 2013/0252280 | A1 | 9/2013 | Weaver |
| 2013/0268290 | A1 | 10/2013 | Jackson et al. |
| 2014/0094588 | A1 | 4/2014 | Meyer |
| 2014/0172442 | A1 | 6/2014 | Broderick et al. |
| 2014/0214391 | A1 | 7/2014 | Cope |
| 2014/0371259 | A1 | 12/2014 | Gold |
| 2015/0019190 | A1 | 1/2015 | Danter |
| 2015/0315657 | A1 | 11/2015 | Rhodes |
| 2016/0034640 | A1 | 2/2016 | Zhao |
| 2017/0147946 | A1 * | 5/2017 | Umeda .................... G06N 7/08 |
| 2018/0260519 | A1 * | 9/2018 | Rietman .................. G16B 5/00 |
| 2019/0057182 | A1 * | 2/2019 | Klement ................ G16H 50/20 |
| 2019/0304568 | A1 * | 10/2019 | Wei ....................... G16B 40/20 |
| 2020/0365231 | A1 * | 11/2020 | Rietman .................. G16B 5/20 |

FOREIGN PATENT DOCUMENTS

| | | | |
|---|---|---|---|
| WO | 2003067217 A2 | 8/2003 | |
| WO | 2005002501 A2 | 1/2005 | |
| WO | 2005004814 A2 | 1/2005 | |
| WO | 2005038618 A2 | 4/2005 | |
| WO | 2009132239 A2 | 10/2009 | |
| WO | 2010144612 A1 | 12/2010 | |
| WO | 2012075069 A2 | 6/2012 | |
| WO | 2013130791 A1 | 9/2013 | |
| WO | WO-2014081882 A2 * | 5/2014 | ............ G16B 30/00 |
| WO | 2014089241 A2 | 6/2014 | |
| WO | 2014152939 A1 | 9/2014 | |
| WO | 2014183078 A1 | 11/2014 | |
| WO | 2014210341 A2 | 12/2014 | |
| WO | 2015048573 A1 | 4/2015 | |
| WO | 2015049688 A2 | 4/2015 | |
| WO | 2015066421 A1 | 5/2015 | |
| WO | 2016011558 A1 | 1/2016 | |
| WO | WO-2016187708 A1 * | 12/2016 | ............ G16B 20/00 |
| WO | WO-2019104428 A1 * | 6/2019 | ............... G16B 5/20 |

OTHER PUBLICATIONS

Weinan, E. et al. The Landscape of complex networks—critical nodes and a hierarchical decomposition. (2013) Methods and applications of analysis, vol. 20 No. 4 p. 383-404. (Year: 2013).*
Peng, J. RNA-seq and Microarrays analyses reveal global differential transcriptomes of Mesorhizobium huakuii 7653R between bacteroids and free living cells. (2014) PLOSONE vol. 9, issue 4 e93626. (Year: 2014).*
Benzekry, S. et al. Design principles for cancer therapy guided by changes in complexity of protein-protein interaction networks. (2015) Biology Direct, vol. 10, 32. (Year: 2015).*
Gnabasik, D. et al. Discrete time evolution of proteomic biomarkers. (2014) IEEE 2014 Int Conference on Computational Science and Computational Intelligence. p. 11-17. (Year: 2014).*
Merelli, E. Topology driven modeling: the IS metaphor. (2015, published online Jun. 24, 2014) Nature Computing, vol. 14 p. 421-430. (Year: 2015).*
Emmett, K. Applying topological principles to genomic analysis. (Oct. 2015) Microbe vol. 10 No. 11 p. 467-474. (Year: 2015).*
International Search Report issued in corresponding application No. PCT/CA2016/050581 dated Aug. 2, 2016 (2 pages).
Written Opinion of the International Searching Authority issued in corresponding application No. PCT/CA2016/050581 dated Aug. 2, 2016 (3 pages).
International Search Report issued in corresponding application No. PCT/CA2016/050586 dated Aug. 29, 2016 (3 pages).
Written Opinion of the International Searching Authority issued in corredponding application No. PCT/CA2016/050586 dated Aug. 29, 2016 (4 pages).
West, et al., "Differential Network Entropy Reveals Cancer System Hallmarks", Nov. 13, 2012, 8 pages.
Dudley, "Biomarker and Drug Discovery for Gastroenterology Through Translational Bioinformatics", Imaging and Advanced Technology, Jan. 1, 2010, 8 pages.
Wu, "A Systems Biology Approach to Identify Effective Drug Cocktail Drugs", BMC Systems Biology, Sep. 20-22, 2009, 14 pages.
Ligeti, "A Network-Based Target Overlap Score for Characterizing Drug Combinations: High Correlation with Cancer Clinical Trial Results", PLOS One, Jul. 31, 2014, 18 pages.
Gonzales-Diaz, "Mind-best: Web Server for Drugs and Target Discovery; Design, Synthesis, and Assay of MAO-B Inhibitors and Theoretical-experimental Study of G3pdh Protein from Trichomonas Gallinae", Journal of Proteome Research, Oct. 5, 2010, 21 pages.
Rietman, "Gibbs Free Energy of Protein-protein Interactions Reflects Tumor Stage", http://dx.dol.org/10.1101/022491, Jul. 13, 2015, 22 pages.
Shannon, "Cytoscape: a Software Environment for Integrated Models of Biomolecular Interaction Networks",Genome Research, Jan. 1, 2003, 7 pages.

(56) References Cited

OTHER PUBLICATIONS

Jiang, "Essential Protein Identification Based on Essential Protein-protein Interaction Prediction by Integrated Edge Weights", Methods 83, Jan. 28, 2015, 12 pages.
Shi, "BMRF-MI: Integrative Identification of Protein Interaction Network by Modeling the Gene Dependency", BMC Genomics, Dec. 4, 2014, 10 pages.
Barbolosi, "Computational Oncology-mathematical Modeling of Drug Regimens for Precision Medicine", www.nature.com/nrclinonc, Apr. 1, 2016, 13 pages.
Baratchart, "Computational Modeling of Metastasis Development in Renal Cell Carcinoma", PLOS Computational Biology, Jun. 11, 2015, 23 pages.
Benzekry, "Modeling Spontaneous Metastasis Following Surgery: an in Vivo-in Silico Approach", Integrated Systems and Technologies: Mathematical Oncology, Oct. 28, 2015, 14 pages.
Xia, "Multidimensional Persistence in Biomolecular Data", Journal of Computational Chemistry, Jan. 1, 2015, 19 pages.
Breitkreutz, "Molecular Signaling Network Complexity is Correlated with Cancer Patient Survivability", PNAS, Jun. 5, 2012, 4 pages.
Benzekry, "Classical Mathematical Models for Description and Prediction of Experimental Tumor Growth", PLOS Computational Biology, Aug. 1, 2014, 19 pages.
Vandin, "Algorithms for Detecting Significantly Mutated Pathways in Cancer", Journal of Computational Biology, Nov. 3, 2011, 16 pages.
Noskov, "Free Energy Decomposition of Protein-protein Interactions", Biophysical Journal, vol. 81, Aug. 1, 2001, 14 pages.
Extended European Search Report dated Feb. 18, 2019 issued in respect of European Patent Application No. 16798990.4 (9 pages).
Dewoskin, D. et al.; "Applications of computational homology to the analysis of treatment response in breast cancer patients". Topology and its Applications, North-Holland, Amsterdam, NL, Jan. 1, 2010, vol. 157, No. 1, pp. 157-164 (8 pages).
Benzekry, Sebastian et al.; "Design principles for cancer therapy guided by changes in complexity of protein-protein interaction networks", Biology Direct, Dec. 1, 2015, vol. 10, No. 1, pp. 32-32 (14 pages).
Rietman, Edward A. et al.; "Thermodynamic measures of cancer: Gibbs free energy and entropy of protein-protein interactions", Journal Of Biological Physics, Kluwer Academic Publishers, Dordrecht, NL, Mar. 24, 2016, vol. 42, No. 3, pp. 339-350 (12 pages).
Andreopoulos, W., et al. "Protein-Protein Interaction Networks", Retrieved from http://www.bioforscher.de/bigM/ippb9076rp8sityx/manager/documents/general/pdf/books/chapters/protein_protein_interaction_networks.pdf on Jan. 1, 2013, (24 pages).
Communication pursuant to Article 94(3) EPC dated Apr. 5, 2022 in European Patent Application No. 16798990.4 (5 pages).
Greenbaum, et al.; "Comparing protein abundance and mRNA expression levels on a genomic scale"; Genome Biology; Aug. 29, 2003; vol. 4, Issue 9, Article 117 (8 pages).
Maier, et al.; "Correlation of mRNA and protein in complex biological samples"; FEBS Letters; Oct. 20, 2009; vol. 583; pp. 3966 to 3973 (8 pages).
The Cancer Genome Atlas Research Network. "Comprehensive molecular characterization of clear cell renal cell carcinoma". Nature; Jun. 23, 2013; 499, pp. 43-49; . https://doi.org/10.1038/nature12222 (7 pages).
The Cancer Genome Atlas Research Network; "Comprehensive genomic characterization defines human glioblastoma genes and core pathways"; Oct. 23, 2008; Nature; vol. 455; pp. 1061-1068 (9 pages).
The Cancer Genome Atlas Network. "Comprehensive molecular characterization of human colon and rectal cancer". Nature 487, 330-337 (Jul. 18, 2012). (8 pages).
The Cancer Genome Atlas Network. "Comprehensive molecular portraits of human breast tumours". Nature 490, 61-70 (Sep. 23, 2012) (10 pages).
The Cancer Genome Atlas Research Network. "Comprehensive genomic characterization of squamous cell lung cancers". Nature 489, 519-525 (Sep. 9, 2012). (8 pages).
The Cancer Genome Atlas Research Network. "Integrated genomic characterization of endometrial carcinoma". Nature 497, 67-73 (May 1, 2013) plus erratum (8 pages).
The Cancer Genome Atlas Research Network. "Integrated genomic analyses of ovarian carcinoma". Nature 474, 609-615 (Jun. 29, 2011) plus erratum (8 pages).
"Genome-wide Molecular Profiles of HCV-lnduced Dysplasia and Hepatocellular Carcinoma" http://www.ncbi.nlm.nih.gov/geo/query/acc.cgi?acc=GSE6764 (accessed Jun. 29, 2022; 2 pages).
Cox, D.R. "Regression Models and Life Tables" Journal of Royal Statistical Society, series B, vol. 34, No. 2, 187-220 (Jan. 1, 1972) (34 pages).

\* cited by examiner

Cluster coefficient

Network size

THERMODYNAMIC MEASURES ON PROTEIN-PROTEIN INTERACTION NETWORKS FOR CANCER THERAPY

BACKGROUND

There is an increasing amount of online bioinformatics data (including but not limited to a human protein-protein (PPI) network, PPI data generally, and transcriptome data) that is not being used by clinicians for therapy. The difficulty is that there is too much information and few relationships between different proteins that have been established.

In a research paper titled "Molecular signaling network complexity is correlated with cancer patient survivability" published by Breitkruetz et al. in 2012 in volume 109 issue 23 of the Proceedings of the National Academy of Sciences, it has been established that complexity of cancer protein-protein interaction (PPI) networks, as measured by degree-entropy, is strongly correlated with cancer patient survival statistics.

Researchers have also suggested that modular bridges and overlaps of protein-protein interaction and signaling networks may be of key importance in drug design. Social association of nodes, perturbation centrality, and centrality measures are used to identify important nodes and substrate binding sites and amino acids participating in allosteric signaling in protein structure networks.

SUMMARY

A computer-implemented method to select a protein target for therapeutic application including the steps of accessing genomic information and protein-protein interaction (PPI) data, the PPI data comprising a network of protein nodes from at least one source, computing, using the genomic information and the PPI data, a thermodynamic measure for each protein node within the network of protein nodes, generating an energy landscape data corresponding to the network of protein nodes and the thermodynamic measure, generating a PPI subnetwork by applying a topological filtration to the energy landscape data of the PPI data, computing a first Betti number for the PPI subnetwork, sequentially removing a first protein node from the PPI subnetwork, computing a second Betti number for the PPI subnetwork with the first protein node removed, computing a change between the first Betti number and the second Betti number, replacing the first protein node into the PPI subnetwork, sequentially removing a second protein node from the PPI subnetwork, wherein the second protein node is different from the first protein node, computing a third Betti number for the PPI subnetwork with the second protein node removed and the first protein node replaced, computing a change between the first Betti number and the third Betti number, and determining, based on the change between the first Betti number and the second Betti number and the change between the first Betti number and the third Betti number, a most significant protein target within the PPI subnetwork.

A computing system that selects a protein target for therapeutic application, including a processing circuitry configured to execute instructions to: access genomic information and protein-protein interaction (PPI) data comprising a network of protein nodes from at least one source, compute, using the genomic information and the PPI data, a thermodynamic measure for each of the protein nodes within the network, generate an energy landscape data corresponding to the network and the thermodynamic measure, generate a PPI subnetwork by applying a topological filtration to the energy landscape of the PPI data, compute a first Betti number for the PPI subnetwork, sequentially remove a first protein node from the PPI subnetwork, compute a second Betti number for the PPI subnetwork with the first protein node removed, compute a change between the first Betti number and the second Betti number, replace the first protein node into the PPI subnetwork, sequentially remove a second protein node different from the first protein node from the PPI subnetwork, compute a third Betti number for the PPI subnetwork with the second protein node removed and first protein node replaced, compute a change between the first Betti number and the third Betti number, and determine, based on the change between the first Betti number and the second Betti number and the change between the first Betti number and the third Betti number, a most significant protein target within the PPI subnetwork, and a display circuitry configured to execute instructions to display the most significant protein target to a user.

A non-transitory computer-readable medium having instructions stored thereon that, in response to execution by the computer system, cause the computer system to perform operations including: computing, using the genomic information and the PPI data, a thermodynamic measure for each of the protein nodes within the network, generating an energy landscape data corresponding to the network and the thermodynamic measure, generating a PPI subnetwork by applying a topological filtration to the energy landscape of the PPI data, computing a first Betti number for the PPI subnetwork, sequentially removing a first protein node from the PPI subnetwork, computing a second Betti number for the PPI subnetwork with the first protein node removed, computing a change between the first Betti number and the second Betti number, replacing the first protein node into the PPI subnetwork, sequentially removing a second protein node different from the first protein node from the PPI subnetwork, computing a third Betti number for the PPI subnetwork with the second protein node removed and first protein node replaced, computing a change between the first Betti number and the third Betti number, determining, based on the change between the first Betti number and the second Betti number and the change between the first Betti number and the third Betti number, a most significant protein target within the PPI subnetwork.

Other aspects and advantages of the invention will be apparent from the following description and the appended claims.

DETAILED DESCRIPTION

Figure 1:
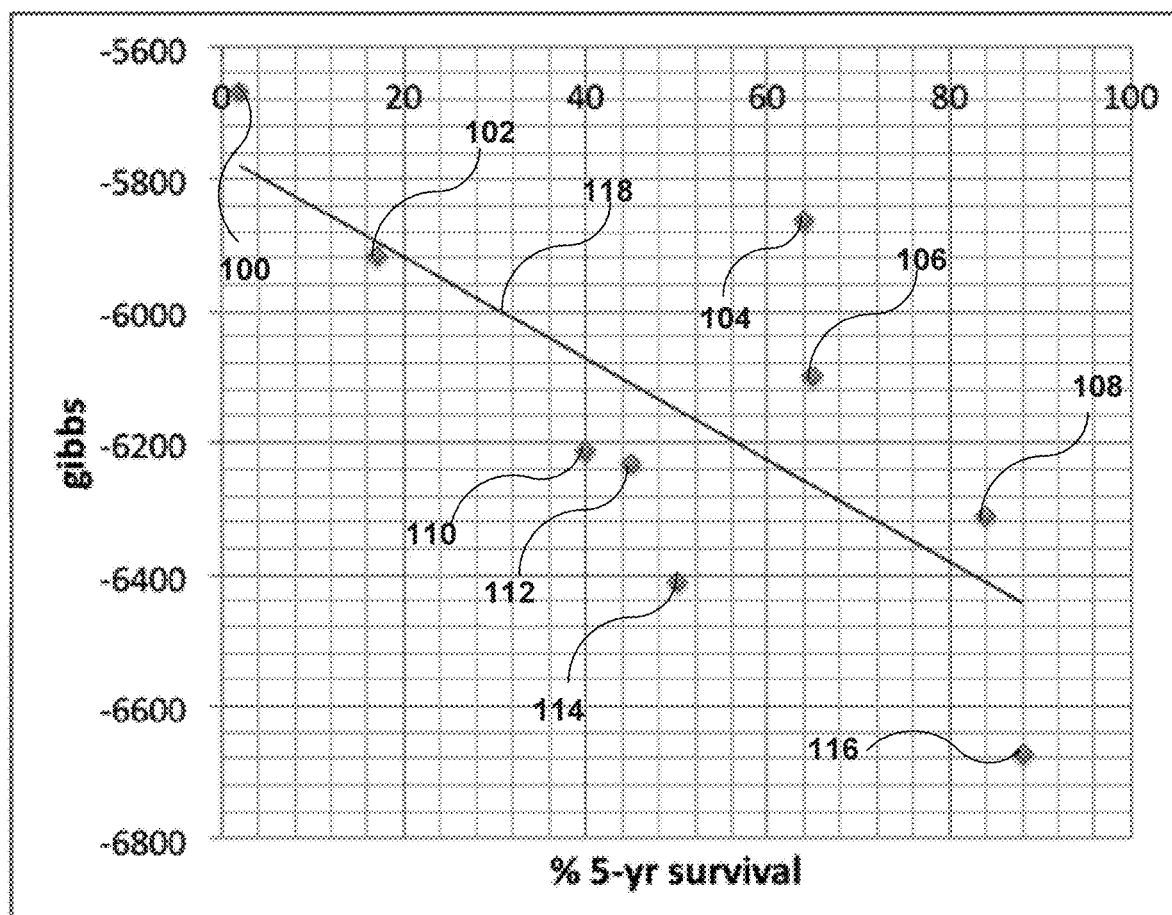
FIGS. 1, 2, and 3 show a graph in accordance with one or more embodiments.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

Throughout the application, ordinal numbers (e.g., first, second, third, etc.) may be used as an adjective for an element (i.e., any noun in the application). The use of ordinal numbers does not imply or create a particular ordering of the elements nor limit any element to being only a single element unless expressly disclosed, such as by the use of the terms "before," "after," "single," and other such terminology. Rather, the use of ordinal numbers is to distinguish between the elements. By way of an example, a lint element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a horizontal beam" includes reference to one or more of such beams.

Terms like "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Although multiple dependent claims are not introduced, it would be apparent to one of ordinary skill in that that the subject matter of the dependent claims of one or more embodiments may be combined with other dependent claims. For example, even though claim 3 does not directly depend from claim 2, even if claim 2 were incorporated into independent claim 1, claim 3 is still able to be combined with independent claim 1 that would now recite the subject matter of dependent claim 2.

In one or more embodiments, a thermodynamic measure is described that allows mapping the molecular pathway, also referred to as the molecular subnetwork or PPI subnetwork, for each patient at each stage of the cancer progression. This allows selection of molecular targets for treatment with a high confidence that the targets have significant meaning for that patient.

In general, embodiments of the invention describe a linear correlation of Gibbs free energy and cancer patient survival. In one or more embodiments, the Gibbs free energy persistent homology on each cancer PPI network is calculated for each patient. Furthermore, the relevant energetic molecular subnetwork, from which another topological measure to compute the Betti (or cycle-basis) number is used, is obtained to select protein targets for inhibition. Because there is a linear correlation with Gibbs free energy, these targets can be selected with confidence.

For example, based on the genetic and phenotypic background of an individual, a different proliferative subnetwork may be engaged in tumor growth. In most cancers, more than one genomic and proteomic alteration is usually identified, resulting in a disadvantage situation where the importance of one molecular alteration over another molecular alteration cannot be easily determined.

An advantage achieved by one or more embodiments compared to conventional therapy is the high confidence for selecting a molecular alteration, also referred to as the most significant target protein(s), that causes the largest effect on the subnetwork when inhibited. It would apparent to one of ordinary skill in the art that the molecular alteration that causes the largest effect on the subnetwork would have the largest impact on inhibiting the progression of the cancer.

In general, the phrase "the most significant protein target(s)" is defined as the protein node(s) in a network or subnetwork that causes the largest change in Betti number when removed. In other words the "most significant" protein target(s) is the number one protein target(s) of choice when administering drugs during therapy.

The following examples and description are for explanatory purposes only and not intended to limit the scope of the invention.

The homeostasis of cells is maintained by a complex, dynamic network of interacting molecules ranging in size from a few dozen Daltons to hundreds of thousands of Daltons. Any change in concentration of one or more of these molecular species alters the chemical balance, or in terms of thermodynamics, chemical potential. These changes then percolate through the network affecting the chemical potential of other species. The end result is perturbations in the network manifesting as concentration changes, giving rise to changes in the energetic landscape of the cell. In the Third Edition of "Physical Chemistry" published by W.H. Freeman and Company in 1986 and in the "Introduction to Theoretical Organic Chemistry" published by Macmillan Company in 1968, authors P. W. Atkins and A. Liberles, respectively, describe these energetic changes as chemical potential on an energetic landscape.

Gene alterations (mutations, variations in expression, translocations, etc.) invariably alter the chemical potential of one or more proteins and/or other molecular species within a single cell. Yet, two neighboring cancer cells in the same microenvironment may exhibit a different energetic landscape because the chemical potential is different within the two cells. Naturally, when a bundle of cells are harvested, for example in a biopsy, and the cells are digested to extract RNA for transcription analysis, the transcriptome is essentially an average of that bundle of cells. Since genes code for proteins, the transcriptome can act as a surrogate for the concentration of the proteins.

To support the conjecture described above, a 2013 publication by Greenbaum et al. on page 117 of volume 4 of *Genome Biology* titled "Comparing protein abundance and mRNA expression levels on a genomic scale" and a 2009 publication by Maier et al. in pages 3966 to 3973 of volume 583 of the *FEBS Letters* titled "Correlation of mRNA and protein in complex biological samples," have described correlations of mRNA with protein concentrations and found Pearson correlation, R, to range from 0.4 to 0.8, in a large number of experiments across five different species. Similarly, as described in a publication titled "Mass-spectrometry-based draft of the human proteome" in pages 582 to 587 of volume 509 of *Nature*, Wilhelm et al. conducted an extensive study on human tissues using both proteomic and mRNA expression and found roughly an 86% correlation between expression and protein concentration.

Data for several cancers from *The Cancer Genome Atlas* (TCGA) hosted by the National Institute of Health (www.cancergnome.nih.gov) have been collected, *The Cancer Genome Atlas* is described by *The TGCA Research*

Network publications in the journal, *Nature*. A set of data that used the Agilent platform G4502A has also been collected and was pre-collapsed on gene symbols. Further, a total of eleven cancers were collected from the following sources: KIRC (kidney renal clear cell) from a 2013 publication by *The TGCA Research Network* titled "Comprehensive molecular characterizations of clear cell renal cell carcinoma," published in pages 43 to 49 of volume 499 of *Nature*; KIRP (kidney renal papillary cell); LGG (low grade glioma); GBM (glioblastoma multiforme) from a 2008 publication by *The TGCA Research Network* titled "Comprehensive genetic characterization defines human glioblastoma genes and core pathways," published in page 1061 of volume 455 of *Nature*; COAD (coloin adenocarcinoma) from a 2012 publication by *The TCGA Research Network* titled "Comprehensive molecular characterization of human colon and rectal cancer," published in pages 330 to 337 of volume 487 of *Nature*; BRCA (breast invasive carcinoma,) from a 2012 publication by *The TGCA Research Network* titled "Comprehensive molecular portraits of human breast tumors," published in pages 61 to 70 of volume 490 of *Nature*; LUAD (lung adenocarcinoma); LUSC (lung squamous cell) from a 2012 publication by *The TGCA Research Network* titled "Comprehensive genomic characterization of squamous cell lung cancers," published in pages 519 to 525 of volume 489 of *Nature*; UCEC (uterine corpus endometrial) from a 2013 publication by *The TGCA Research Network* titled "Integrated genomic characterization of endometrial carcinoma," published in pages 67 to 73 of volume 497 of *Nature*; OV (ovarian serous cystadenocarcinoma) from a 2012 publication by *The TGCA Research Network* titled "Integrated genomic analysis of ovarian carcinoma," published in pages 609 to 615 of volume 476 of *Nature*; READ (rectum adenocarcinoma).

In one or more embodiments, two databases for survival data are used. The first database is the Surveillance Epidemiology and End Results (SEER) National Cancer Institute database, which contains detailed statistical information about the five-year survival rates of patients with cancer. The second database is the National Brain tumor Society database. While these two databases may be used, a single database or multiple other databases could be used that provide the same or equivalent data.

FIG. 1 shows a graph in accordance to one or more embodiments. In one or more embodiments, FIG. 1 shows the application of the TCGA data described above. As seen in FIG. 1, the 5 year survival rate and correlating Gibbs free energy number for the different cancers: glioblastoma multifome (GMB) (100), lung adenocarcinoma (LUAD) (102), rectum adenocarcinoma (READ) (104), colon adenocarcinoma (COAD) (106), uterine corpis endometrial (UCEC) (108), lung squamous cell (LUSC) (110), ovarian serous cystadenocarcinoma (UCEC) (112), low grade glioma (LGG) (114), and breast invasive glioma (BRCA) (116) are plotted. The y-axis in FIG. 1 is the Gibbs energy shown in an arbitrary scale and the x-axis represents the probability of 5-year patent survival.

As seen in FIG. 1, a linear correlation (116) exists between overall Gibbs free energy and 5-year survival rate. This result demonstrates that the probability of 5-year patient survival is inversely proportional to the complexity of the signaling network (measured by Gibbs energy) for the types of cancer considered. Other measures of network complexity, such as degree-entropy, number of leaf nodes, and/or cyclomatic number have also been found to inversely correlate with 5 year survival. These results indicate the existence of a correlation between the probability of survival (clinical data) and the complexity of signaling networks (mathematical inference). Furthermore, these results also imply that the inactivation of certain protein targets (e.g. those that can reduce network complexity) can bring about reduction in cancerous growth and increase in survival.

Figure 2:
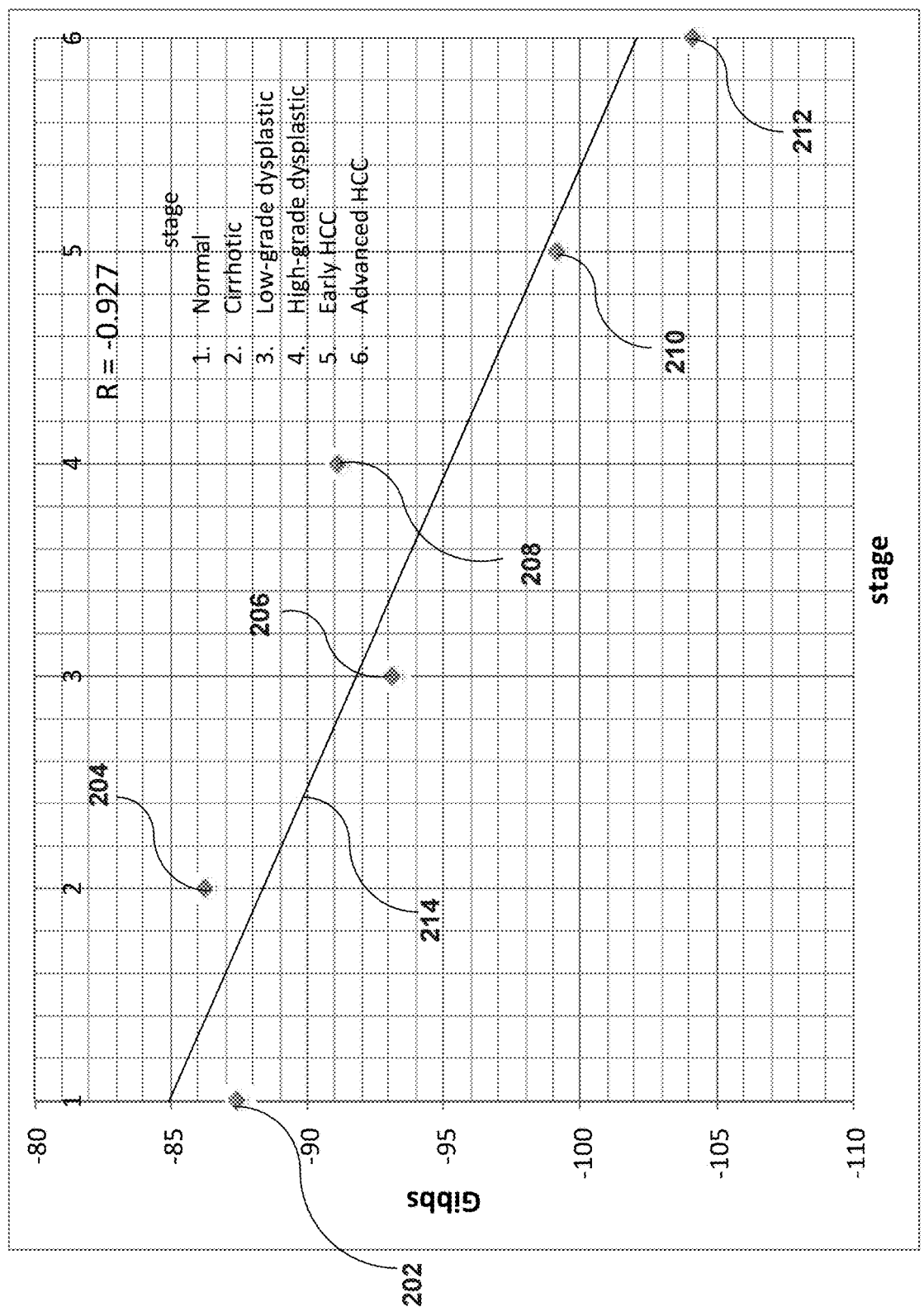

FIG. 2 shows a graph in accordance with one or more embodiments. In one or more embodiments, FIG. 2 is a graph that shows the Gibbs free energy correlation with cancer stage for liver cancer. As shown in FIG. 2, the cancer stages: normal tissue (202), cirrhotic stage (204), low-grade dysplastic (206), high-grade dysplastic (208), early HCC (210), and advanced HCC (212) are assigned to an ordinal number of 1 through 6 and plotted on the x-axis. In FIG. 2, the y-axis is the Gibbs energy on an arbitrary scale In FIG. 2 gene expression data from GSE6764 was normalized so as to be in the range of [0,1] and overlaid on a protein-protein interaction network from Biogrid® using Gibbs free energy equations described later in one or more embodiments. In FIG. 2, the Pearson correlation is −0.927, the Spearman correlation of the mean Gibbs free energy for the individual cancer stages is R=−0.99 with a p-value of 0.0001, and the Kendall's tau correlation is 1.000, with a p-value of 0.0016.

As seen in FIG. 2, a linear correlation (214) exists between the Gibbs free energy and the cancer stages when the cancer stages are assigned to an ordinal number. While other protein-protein interaction network measures may have been found to correlate with survival, the finding of a linear correlation between Gibbs energy and cancer stage as shown in FIG. 2 is a new discovery. The results in FIG. 2 provides an additional level of reassurance that changes in network complexity are relevant to cancer progression, because the complexity of each cancer specific protein interaction network can be described by quantifying the energy of the connections within the protein interactions. Therefore, if a decrease in network complexity can be correlated with lower cancer stage, then the identification of nodes (proteins) which produce significant reduction in network complexity can pinpoint the most appropriate therapeutic target.

In one or more embodiments, the Gene Expression Omnibus (GEO) at www.ncbi.nlm.nih.gov is accessed for transcription data relevant to prostate and liver carcinoma. The data for the liver cancer study (hepatocellular carcinoma) was GSE6764, and the prostate study GSE3933 and GSE6099. The GSE3933 and GSE6099, as obtained, were log(2) processed and collapsed to gene IDs. The data was modified to gene cluster text (.gct) file format and processed with GenePattern® at Broad Institute. The expression data for liver cancer, GSE6764, was in an Affymetrix® format (HG_U133_Plus_2 probe set), and also preprocessed to collapse them into gene IDs.

Figure 3:
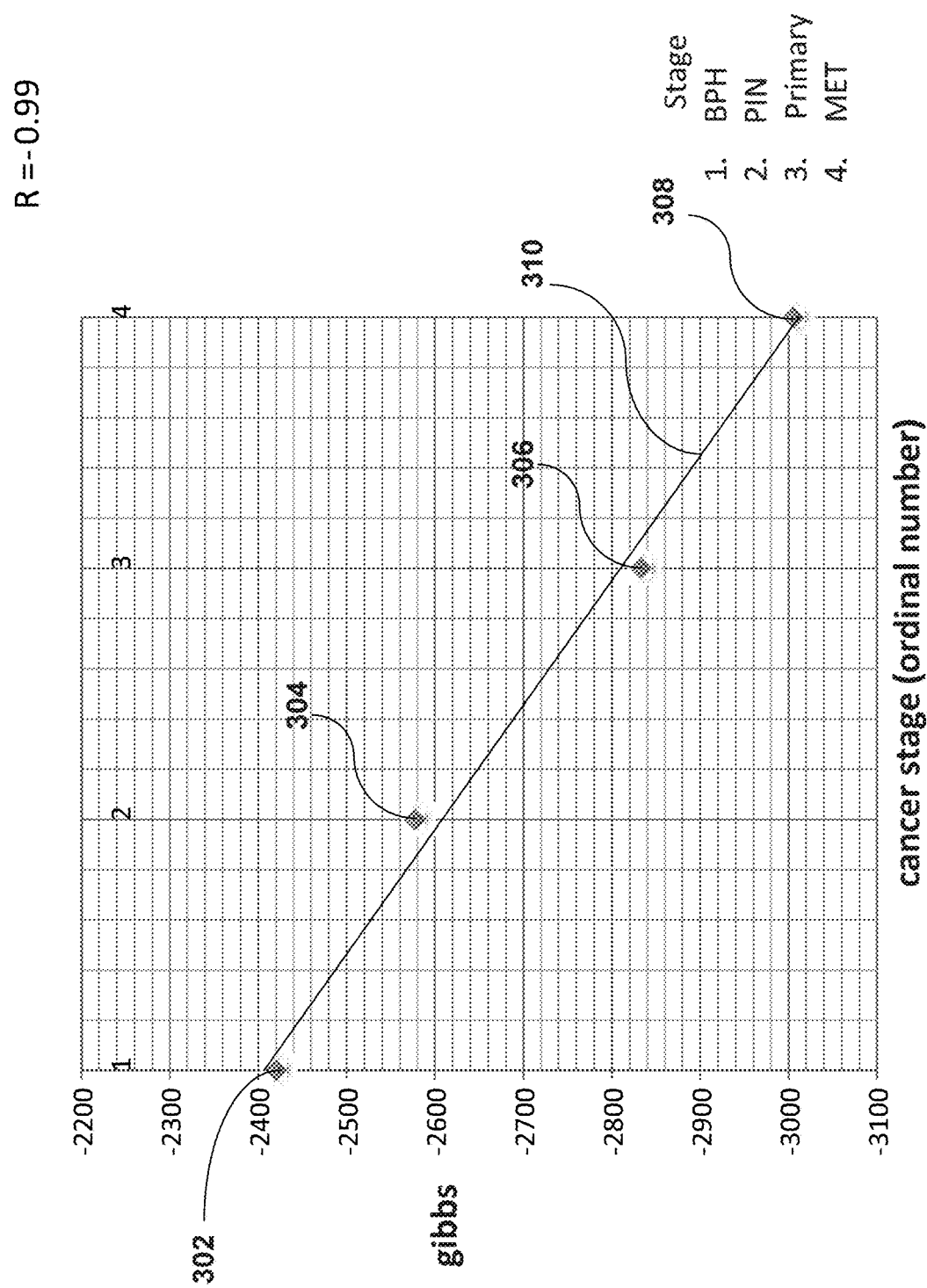

Similarly, FIG. 3 shows a graph in accordance with one or more embodiments. In one or more embodiments, FIG. 3 is a graph showing the Gibbs energy correlating with cancer stage, more specifically, Gibbs free energy vs. cancer stage for prostate cancer. As shown in FIG. 3, the prostate cancer stages: normal benign prostate hypoplasia (BPH) (302), prostatic interepithelial neoplasia (PIN) (304), primary tmor (Primary) (306), and metastatic (MET) (308) are assigned to an ordinal number of 1 through 4 and plotted on the x-axis. In FIG. 3, the y-axis is the Gibbs energy on an arbitrary scale. In one or more embodiments, for the calculation of FIG. 3 gene expression data from GSE3933 and GSE6099 were normalized so as to be in the range of [0,1] and overlaid on Biogrid® protein-protein interaction network using Gibbs free energy equations described later in one or more embodiments. In FIG. 3, the Spearman R correlation is −1.000 with p-value.

As seen in FIG. 3, a linear correlation (310) exists between the Gibbs free energy and the cancer stages when the cancer stages are assigned to an ordinal number. As described above in FIG. 2, the identification of protein hubs that most contribute to network complexity (most energetic nodes) is likely to pinpoint putative molecular targets for therapy. Carefully choosing a minimum set of protein targets to be inhibited, according to the subnetwork energy, can result in a X % decrease in the calculated network complexity (measured by Gibbs energy), and can double the predicted rate of 5-year survival or reduce cancer stage.

It would be apparent to one of ordinary skill in the art that given that the data for these calculations come from such diverse sources it is highly suggestive that the correlations are good. This suggests exploiting the Gibbs energy concept for target selection.

Figure 4:
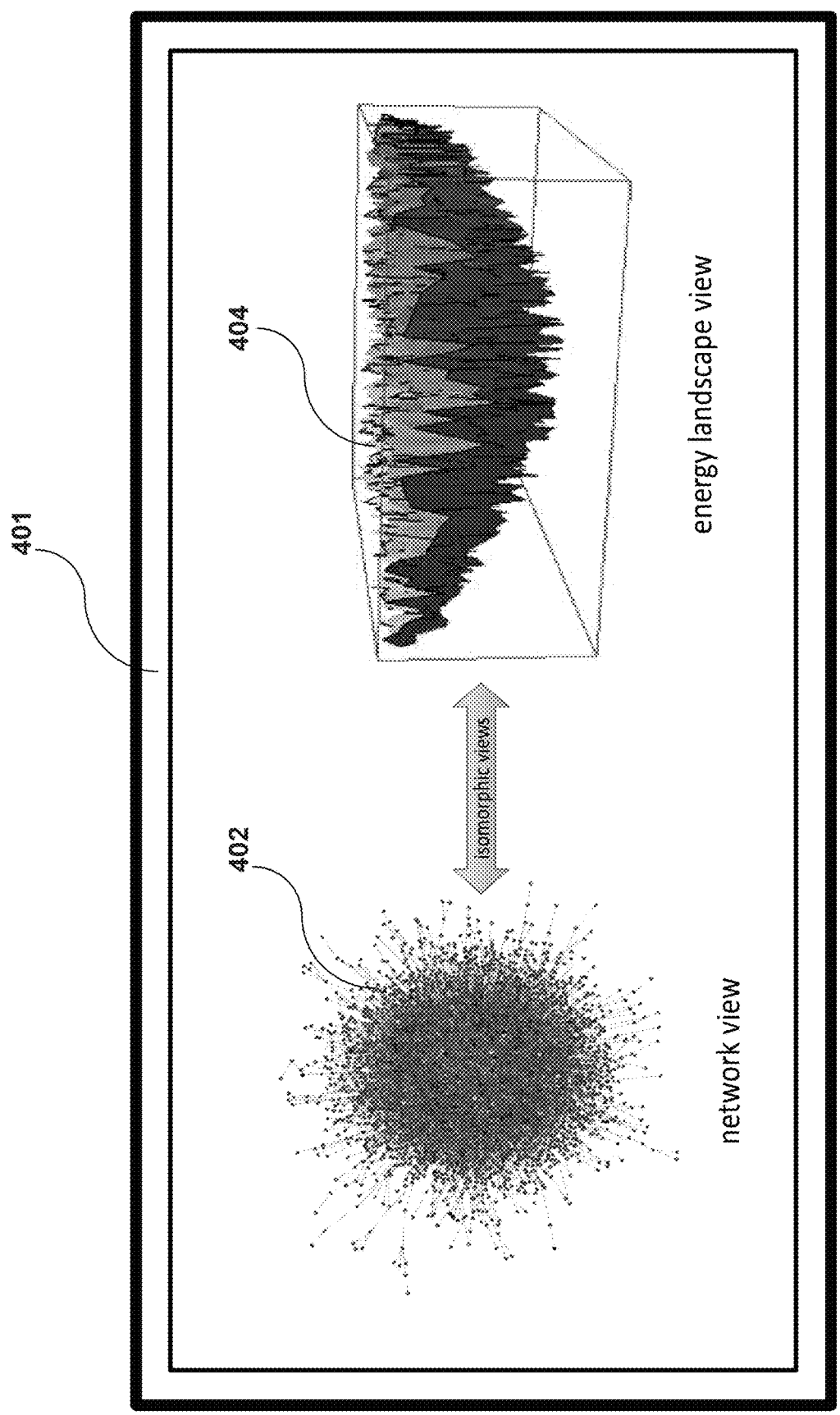
FIG. 4 shows diagrams in accordance with one or more embodiments.

FIG. 4 shows diagrams in accordance with one or more embodiments. In one or more embodiments, once a Gibbs free energy is assigned to each node in a PPI network, the PPI network can then be viewed as a rugged landscape (402) within, for example, a graphical user interface (GUI) (401) as depicted in FIG. 4. In one or more embodiments of the invention, the GUI and one or more display devices for viewing the GUI is shown and described in relation to FIG. 10A. Returning to FIG. 4, the network with real numbers attached to each node is isomorphic to an energy landscape (404), which in one or more embodiments is displayed within the GUI (401). A topological "filtration" technique can be applied to the energy landscape (404) to extract a "persistent homology."

In one or more embodiments, the human PPI network (Homo sapiens, 3.3.99, March, 2013) from BioGrid (www.thebiogrid.org), which contains 9561 nodes and 43,086 edges, was used. The entire human PPI was loaded into version 2.8.1 of Cytoscape. In a publication by Shannon et al. titled "Cytoscape: A softward environment for integrated models of bimolecular interaction networks," published in 2013 in pages 2498 to 2504 of volume 13 issue 11 of *Genome Research*, Shannon et al. describes the general application and use of the Cytoscape software. The list of genes obtained from TCGA (full-length expression set was 17,814 genes) for a specific cancer was "selected" using the Cytoscape functions, the "inverse selection" of Cytoscape function applied, and the nodes and genes edges were removed. The resulting network, which now included only those genes found in both Biogrid and TCGA, consisted of 7951 nodes and 36,509 edges. This Cytoscape network was unloaded as an adjacency list for processing by custom Python code using version 2.6.4 of Python with appropriate NetworkX functions.

In one or more embodiments the RNA (e.g., mRNA, rRNA, tRNA, and other non-coding RNA) transcriptome value as a surrogate for protein concentration can be "overlaid" on a PPI network, such as the human PPI at Biogrid (www.biogrid.org) shown as the rugged landscape (402) in FIG. 4. Once the RNA transcriptome value has been overlaid, the log(2) transformed transcription data is first rescaled to be in the range [0,1]. In one or more embodiments, the most highly, positively expressed value will be set to 1.0 and the most negatively, down-regulated value will be set to 0.

It would be apparent to one of ordinary skill in the art that this is comparable to stating that the most strongly up-regulated gene produces a protein of very great concentration, relative to the most strongly down-regulated gene that result in the lowest protein concentration.

In one or more embodiments, the corresponding rescaled transcriptome data is assigned to each protein in the PPI network. The following equation is then used to compute the Gibbs free energy for that protein:

$$G_i = c_i \ln \frac{c_i}{\sum_{j=i} c_j} \qquad \text{Eq. [1]}$$

In one or more embodiments, it is assumed that the protein of interest is i with concentration, ci. This concentration is the rescaled transcription data for that gene. In the denominator of the argument to the natural logarithm the summation is taken over concentrations (rescaled) for all the neighbors to the protein of interest, i. This is essentially the Gibbs free energy, Gi, for that protein in the PPI network.

In one or more embodiments, the overall Gibbs free energy of the PPI network can be obtained using the equation of:

$$qG = \sum_i G_i \qquad \text{Eq. [2]}$$

In one or more embodiments, Equation [2] represents the Gibbs free energy for a patient. In one or more embodiments, Equation [2] may also represent the different cancer stages for patients, depending on when the biopsy was taken.

Figure 5C:
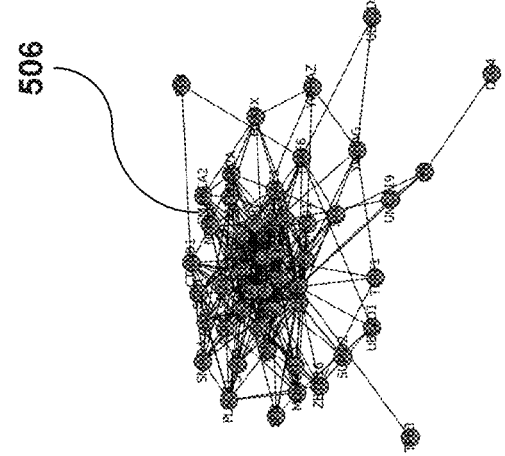
FIGS. 5A, 5B, 5C, and 5D show diagrams in accordance with one or more embodiments.
Figure 5D:
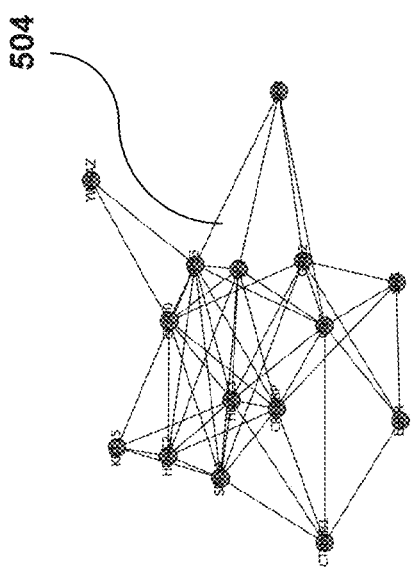
Figure 5A:
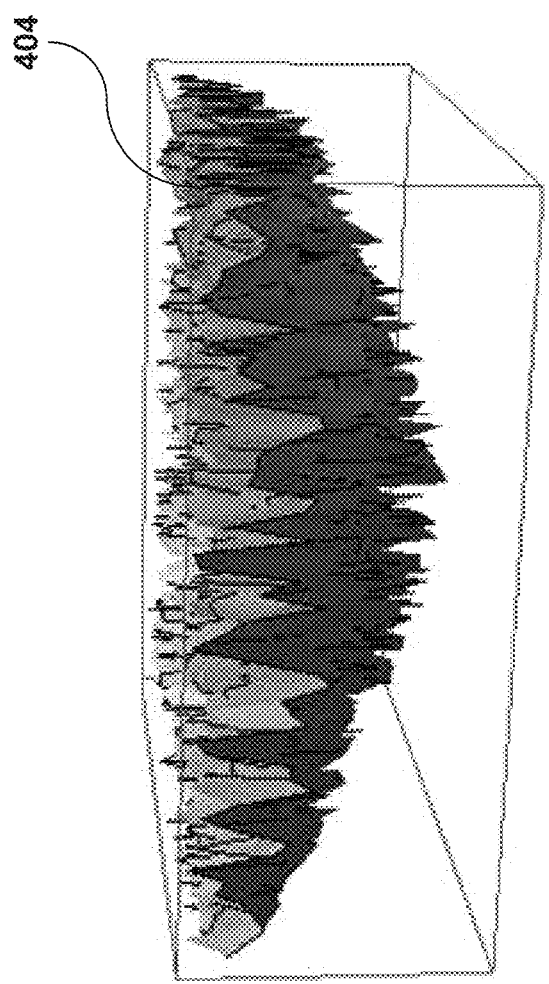
Figure 5B:
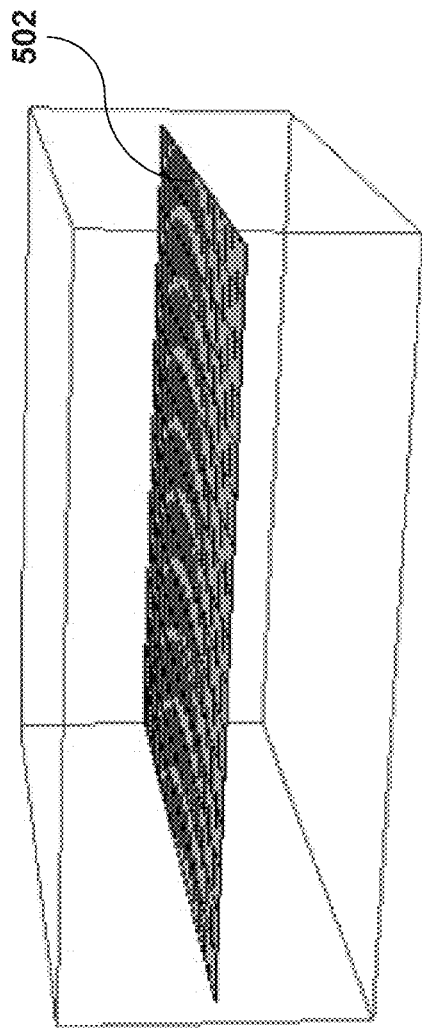

FIGS. 5A, 5B, 5C, and 5D show diagrams in accordance with one or more embodiments. In one or more embodiments, shown in FIG. 5A, an energy landscape (404) is shown. In one or more embodiments, shown in FIG. 5B, a topological filtration (502), also referred to as a filtration threshold, can be moved up from far below the lowest minima on an energy landscape (404). As the filtration threshold is moved up further, small connected subnetworks (504) as shown in FIG. 5D, and later larger connected subnetworks (506) as shown in FIG. 5C are revealed. These subnetworks are known as persistent homology.

As shown in FIGS. 5C and 5D, it would be apparent to one of ordinary skill in the art that as the filtration threshold is increased, the complexity of the subnetwork is also increased.

In one or more embodiments, if the normalized or rescaled, expression data were assigned as real numbers a persistent homology cannot be obtained when the topological filtration is applied. The nodes will be disconnected until a threshold of several hundred. In contrast, by using the normalized or rescaled, expression data, a threshold as low as 5 and as high as 7000 gives a smooth change in network measure on the subnetworks.

Figure 6A:
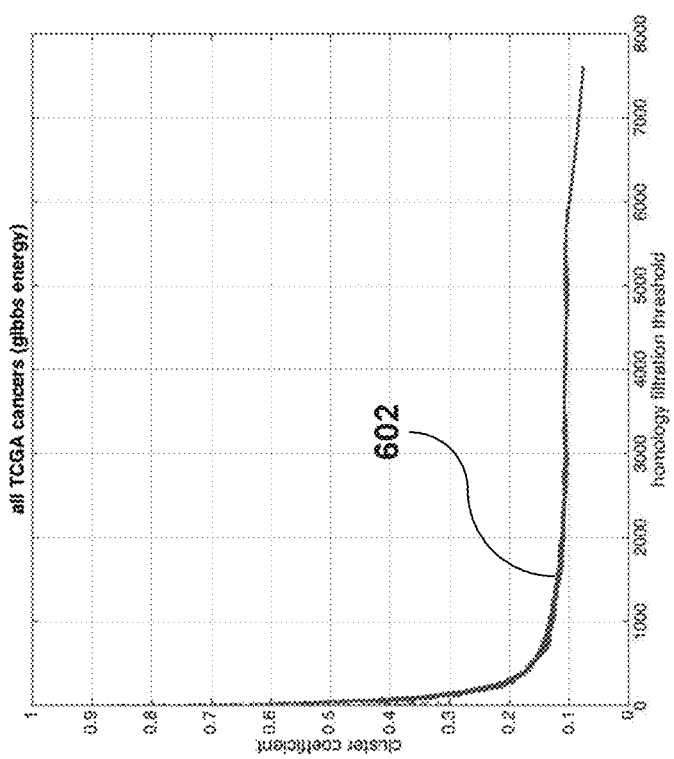
FIGS. 6A and 6B show a graph in accordance with one or more embodiments.
Figure 6B:
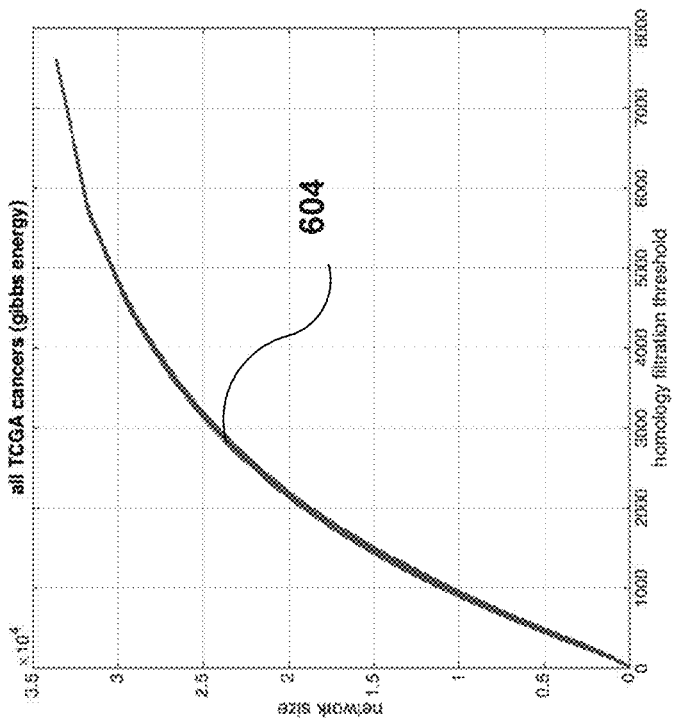

FIGS. 6A and 6B shows a graph in accordance with one or more embodiments. In one or more embodiments, the graph in FIG. 6A shows the cluster coefficient and the graph in FIG. 6B shows the cluster size of the persistent homology subnetworks as a functions of the filtration threshold. As shown in the first curve (602) in FIG. 6A and the second curve (604) in FIG. 6B, no apparent kinks are shown that would represent a phase transition as the filtration threshold is increased from 1 to 7000.

In one or more embodiments, to demonstrate how the subnetworks are used for targeting and treatment of individual patients, the TCGA glioblastoma multiforme (GBM) data is used as an example.

Figure 13:
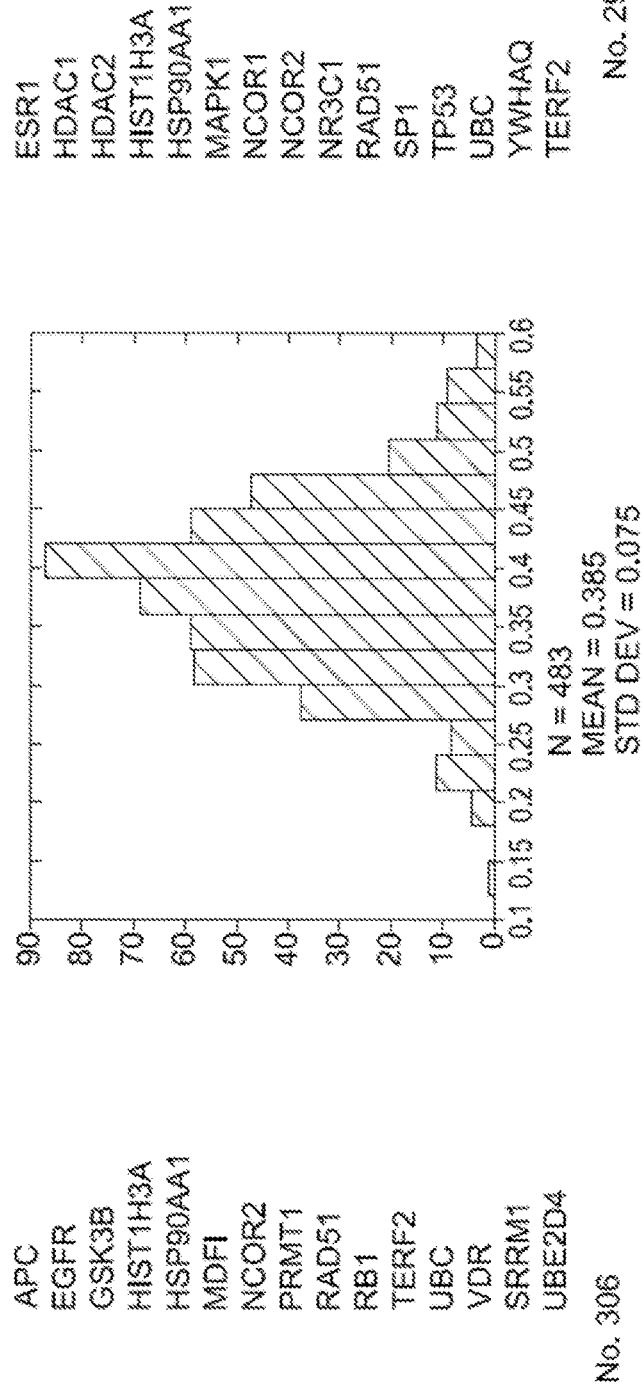
FIG. 13 shows diagrams in accordance with one or more embodiments.
Figure 13:
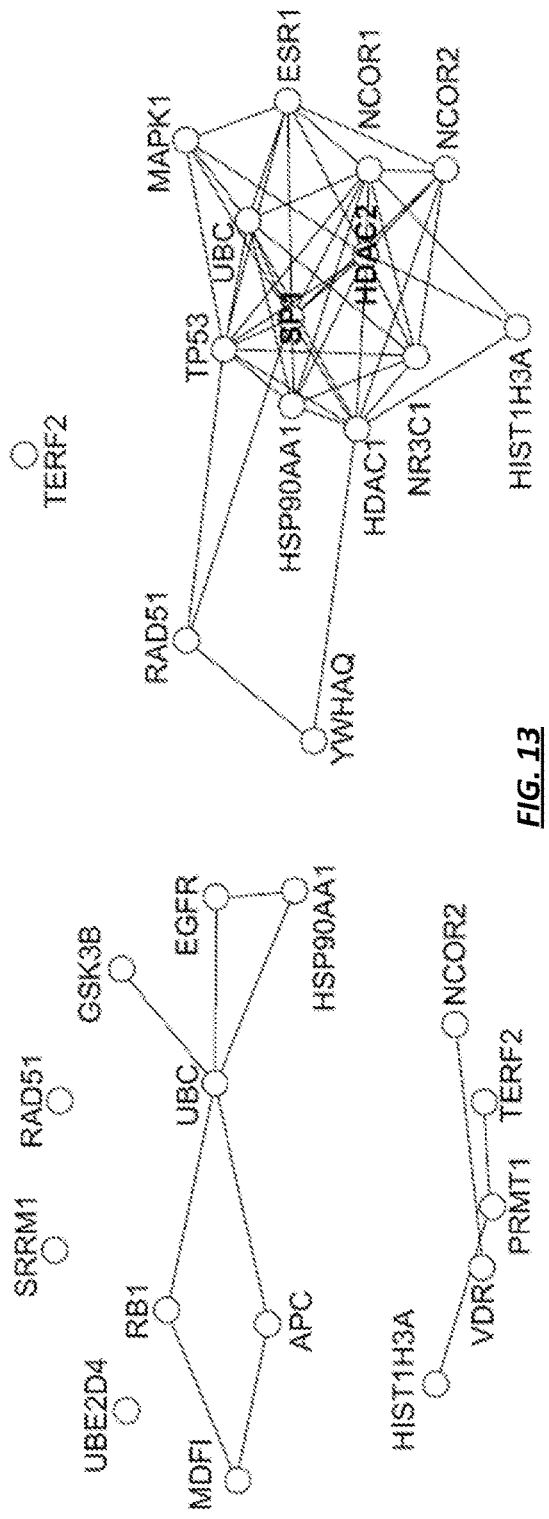

In one or more embodiments, FIG. 13 shows a histogram for a network metric known as closeness centrality, which measures the mean distance from a node in the network to all other nodes, on 483 GBM patients. The Gibbs energy persistent homology for the individual patient was first computed, and the closeness centrality for subnetworks at a filtration threshold of 15 was then computed. In one or more embodiments, the histogram in FIG. 13 shows the full range of closeness centrality and thus the differences in subnetworks for each patient.

As shown in FIG. 13, the graph in the center presents the distribution of closeness-centrality (the x-axis) vs. the number of subnetworks at a filtration threshold of 15 (the y-axis). On the left of the graph, a list of genes with the respective subnetwork is provided. This subnetwork represents an example of the least connected network (e.g. one that has the lowest closeness-centrality of the population of graphs). On the right of the graph, another list of genes with the respective subnetwork is provided. In contrast to the list of genes on the left, the list of genes provided on the right contains the most connected network (e.g, the highest closeness-centrality of the population of graphs).

In one or more embodiments, the distribution study as shown in FIG. 13 refers to a population of patients and therefore identifies frequency of specific homology subnetworks within a population of patients with specific type of cancer and guide drug treatment for the majority of patients vs rare molecular subtypes.

In one or more embodiments, the subnetworks can be used to compute drug targets. First, the Gibbs energy of the subnetwork is demonstrated as significant, in relation to survival of GBM patients. In one or more embodiments, a Cox proportional hazards (Cox PH) model is used to show this significance.

The Cox proportional hazards is described by Cox in a 1972 publication titled "Regression Models and Life Tables" in pages 187 to 220 in series B, volume 34, No. 2 of the *Journal of Royal Statistical Society*.

In a research paper titled "Molecular signaling network complexity is correlated with cancer patient survivability" published in 2012 in volume 109 issue 23 of the *Proceedings of the National Academy of Sciences*, Breitkruetz et al. shows that the model was constructed from several statistical and thermodynamic measures on the Gibbs subnetwork at threshold of 32. The statistical measures included: number of edges, transitivity, and clique.

Furthermore, a topological measure known as the Betti number is used. The Betti number is described by Benzekry et al. in a publication titled "Design Principles for Cancer Therapy guided by changes in complexity of Protein-Protein Interaction Networks." The Betti number calculates the number of rings of four or more nodes in the PPI network, in this case the Gibbs homology subnetworks.

These six parameters (i.e. number of edges, transitivity, clique, degree-entropy, Betti number, Gibbs energy of the subnetwork) are fitted into the Cox PH model. The Chi Square probability for the overall model is 0.0426 and the most important parameter is the Gibbs energy of the subnetwork with a Chi Square fitting probability of 0.0026. Furthermore, fitting only to days-to-death with gibbs-subnetwork energy in log-logistic model, a Chi square of <0.0001 is obtained.

In one or more embodiments, the Betti number and the Gibbs energy for this subnetwork is calculated. It would be apparent that since Betti number and Gibbs free energy correlates linearly with survival for different cancers, it is possible to inhibit a protein at different stages of the cancer that gives the largest drop in Betti number with high confidence that the complexity of the subnetwork has been reduced.

In one or more embodiments, whether or not the complexity has been reduced can be double checked to see if the Gibbs free energy has increase. In one or more embodiments, this is done on a patient-to-patient basis. It would be apparent to one of ordinary skill in the art that the method of one or more embodiments, referred to as the Gibbs-Betti method, can generate an energetic subnetwork for each patient no matter the cancer stage. Furthermore, the gibbs-betti method of one or more embodiments can be used to identify a specific drug target for each patient.

Figure 7:
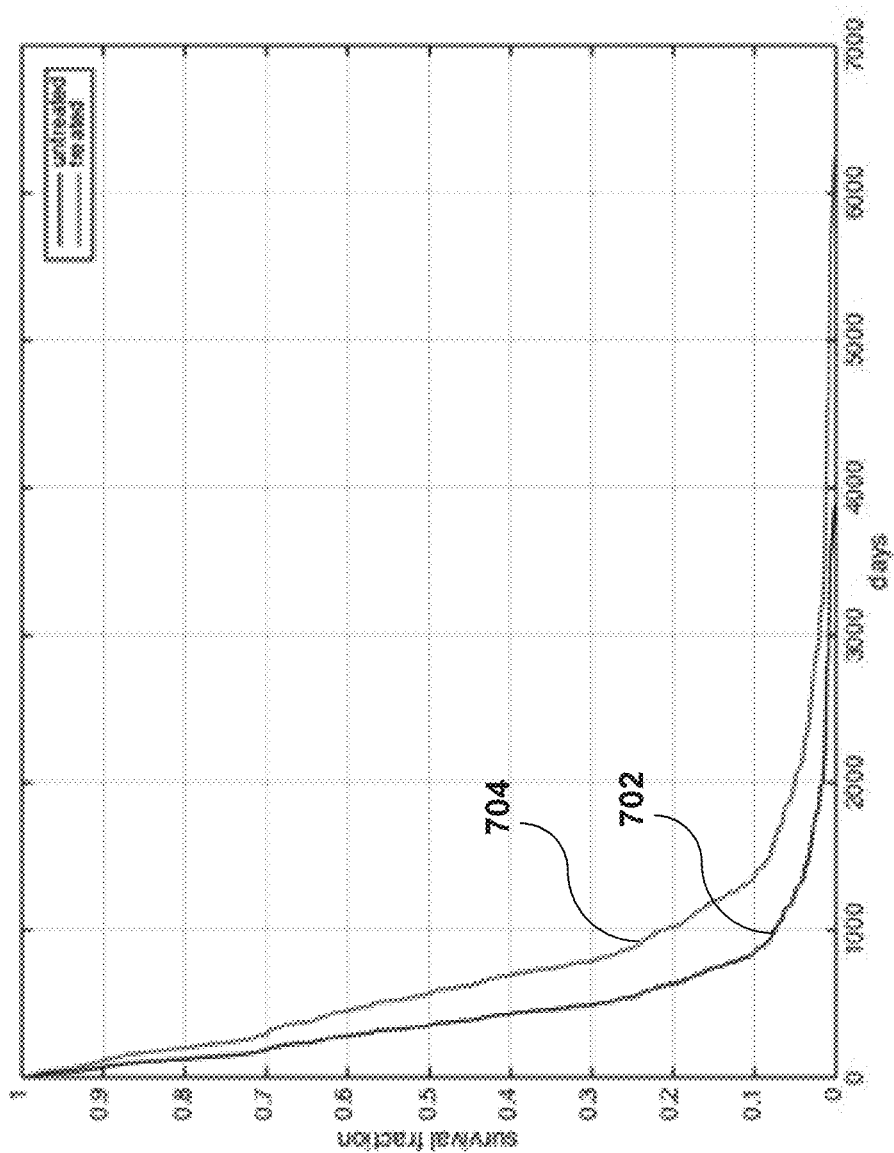
FIGS. 7, 8, and 9 show a graph in accordance with one or more embodiments.

FIG. 7 shows a graph according to one or more embodiments. In one or more embodiments, FIG. 7 shows a hazard model: a fit of days-to-death with Gibbs energy for the homology subnetworks at threshold 32 for glioblastoma (using the same TCGA data), which is also referred to as a log-logistic fit. The lowest curve (702) represents the untreated patients, and the upper curve (704) is a simulation of patients treated with targeted agents that inhibit the proteins identified using the Gibbs-homology (threshold 32) and Betti number method as described above in one or more embodiments. The x-axis represents number of days to death (from TCGA), and the y-axis is survival fraction (or probability of survival).

From the results shown in the graph of one or more embodiments in FIG. 7, it would be apparent to one of ordinary skill in the art that the patients treated with the Gibbs-Betti method of one or more embodiments survived longer than the conventionally treated patients.

Figure 8:
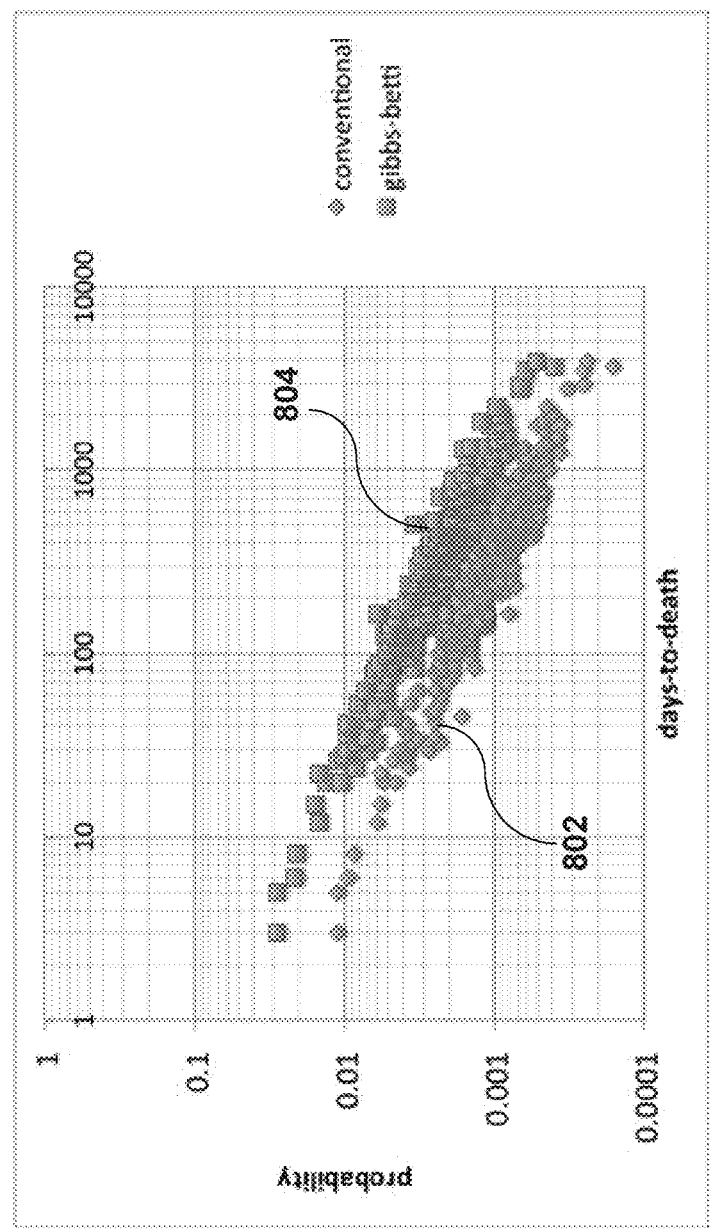

FIG. 8 shows a graph according to one or more embodiments. As seen in FIG. 8, the log-logistic for glioblastoma patients as shown in FIG. 7 treated with conventional therapy (802) and glioblastoma patients with a simulated treatement based on the Gibbs-Betti method (804) of one or more embodiments are compared. The overall improvement of the Gibbs-Betti method (804) of one or more embodiments compared to the results for conventional therapy (802) is estimated at 134%.

Figure 9:
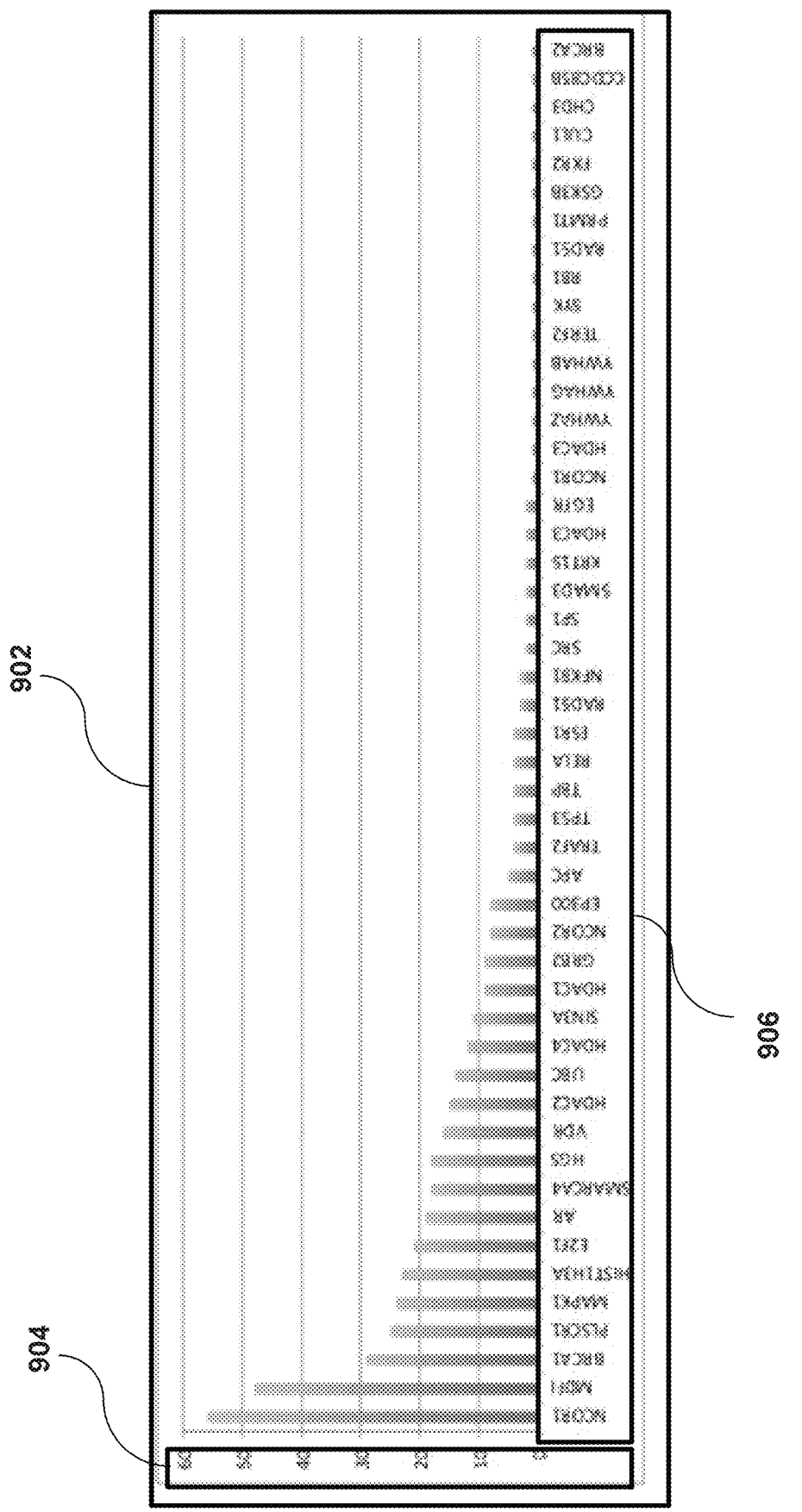

FIG. 9 shows a graph in accordance with one or more embodiments. FIG. 9 shows a Pareto chart (902) of the best targets for individual patients (904) with glioblastoma carcinoma. The chart shows that the best protein target among the plurality of protein targets (906) was NCOR1 for 56 patients. The chart also shows that MDF1 was the best target for 48 patients.

Figure 10B:
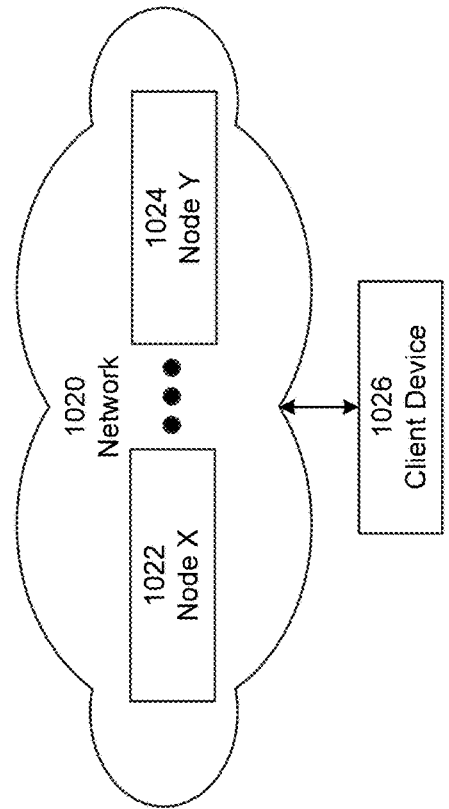
FIGS. 10A and 10B show a computing system in accordance with one or more embodiments.
Figure 10A:
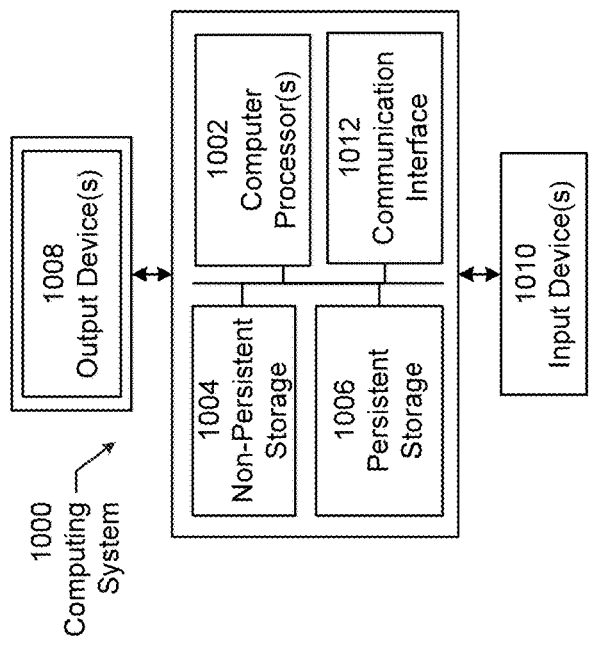

FIGS. 10A and 10B show a computing system in accordance with one or more embodiments of the technology.

Embodiments of the invention may be implemented on a computing system. Any combination of mobile, desktop, server, router, switch, embedded device, or other types of hardware may be used. For example, as shown in FIG. 10A, the computing system (1000) may include one or more computer processors (1002), non-persistent storage (1004) (e.g., volatile memory, such as random access memory (RAM) cache memory), persistent storage (1006) (e.g., a hard disk, an optical drive such as a compact disk (CD) drive or digital versatile disk (DVD) drive, a flash memory, etc.), a communication interface (1012) (e.g., Bluetooth interface, infrared interface network interface, optical interface, etc.), and numerous other elements and functionalities.

The computer processor(s) (1002) may be an integrated circuit for processing instructions. For example, the computer processor(s) may be one or more cores or micro-cores of a processor. The computing system (1000) may also include one or more input devices (1010), such as a touchscreen, keyboard, mouse, microphone, touchpad, electronic pen, or any other type of input device.

The communication interface (1012) may include an integrated circuit for connecting the computing system (1000) to a network (not shown) (e.g., a local area network (LAN), a wide area network (WAN) such as the Internet, mobile network, or any other type of network) and/or to another device, such as another computing device.

Further, the computing system (1000) may include one or more output devices (1008), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (1002), non-persistent storage (1004), and persistent storage (1006). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the invention.

The computing system (1000) in FIG. 10A may be connected to or be a part of a network. For example, as shown in FIG. 10B, the network (1020) may include multiple nodes (e.g., node X (1022), node Y (1024)). Each node may correspond to a computing system, such as the computing system shown in FIG. 10A, or a group of nodes combined may correspond to the computing system shown in FIG. 10A. By way of an example, embodiments of the invention may be implemented on a node of a distributed system that is connected to other nodes. By way of another example, embodiments of the invention may be implemented on a distributed computing system having multiple nodes, where each portion of the invention may be located on a different node within the distributed computing system. Further, one or more elements of the aforementioned computing system (1000) may be located at a remote location and connected to the other elements over a network.

Although not shown in FIG. 10B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (1022), node Y (1024)) in the network (1020) may be configured to provide services for a client device (1026). For example, the nodes may be part of a cloud computing system. The nodes may include functionality to receive requests from the client device (1026) and transmit responses to the client device (1026). The client device (1026) may be a computing system, such as the computing system shown in FIG. 10A. Further, the client device (1026) may include and/or perform all or a portion of one or more embodiments of the invention.

The computing system or group of computing systems described in FIGS. 10A and 10B may include functionality to perform a variety of operations disclosed herein. For example, the computing system(s) may perform communication between processes on the same or different system. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, only one authorized process may mount the shareable segment, other than the initializing process, at any given time.

Other techniques may be used to share data, such as the various data described in the present application, between processes without departing from the scope of the invention. The processes may be part of the same or different application and may execute on the same or different computing system.

Rather than or in addition to sharing data between processes, the computing system performing one or more embodiments of the invention may include functionality to receive data from a user. For example, in one or more embodiments, a user may submit data via a GUI on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered in the web client and displayed on the user device.

Once data is obtained, such as by using techniques described above or from storage, the computing system, in performing one or more embodiments of the invention, may extract one or more data items from the obtained data. For example, the extraction may be performed as follows by the computing system in FIG. 10A. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail—such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query presented to a structured data repository (where the data repository may be organized according to a database schema or data format, such as XML).

The extracted data may be used for further processing by the computing system. For example, the computing system of FIG. 10A, while performing one or more embodiments of the invention, may perform data comparison. Data comparison may be used to compare two or more data values (e.g., A, B). For example, one or more embodiments may determine whether A>B, A=B, A!=B, A<B, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if A>B, B may be subtracted from A (i.e., A−B), and the status flags may be read to determine if the result is positive (i.e., if A>B, then A−B>0). In one or more embodiments, B may be considered a threshold, and A is deemed to satisfy the threshold if A=B or if A>B, as determined using the ALU. In one or more embodiments of the invention, A and B may be vectors, and comparing A with B requires comparing the first element of vector A with the first element of vector B, the second element of vector A with the second element of vector B, etc. In one or more embodiments, if A and B are strings, the binary values of the strings may be compared.

The computing system in FIG. 10A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 10A may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be presented through various audio methods. In particular, data may be rendered into an audio format and presented as sound through one or more speakers operably connected to a computing device.

Data may also be presented to a user through haptic methods. For example, haptic methods may include vibrations or other physical signals generated by the computing system. For example, data may be presented to a user using a vibration generated by a handheld computer device with a predefined duration and intensity of the vibration to communicate the data.

The above description of functions present only a few examples of functions performed by the computing system of FIG. 10A and the nodes and/or client device in FIG. 10B. Other functions may be performed using one or more embodiments of the invention.

Figure 11:
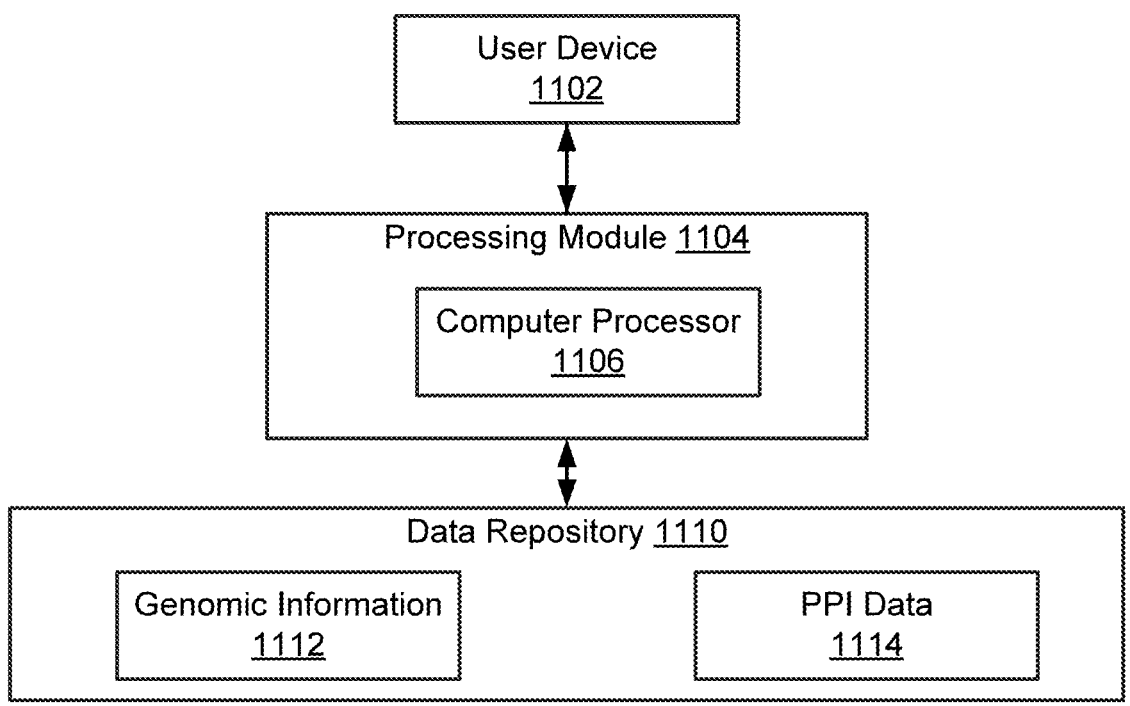
FIG. 11 shows a schematic diagram in accordance with one or more embodiments.

FIG. 11 shows a schematic diagram of a system in accordance with one or more embodiments. The system for selecting a protein target for therapeutic application includes (i) a processing module (1104) including a computer processor (1106) configured to execute instructions configured to: access genomic information (transcription/gene expression analysis, rare transcript, splice variant or fusion transcript on any of the present or future analytic platforms) associated with a patient, access PPI data from one or more reference human (academic, public or private) PPI networks, compute, using the genomic information and the PPI data, a thermodynamic or mathematical measure, and determine, from the thermodynamic or mathematical measure, a protein target within the PPI data; and (ii) a user device (1102) configured to present the protein target to a user. The system may further include a data repository (1110) configured to store the genomic information (1112) and the PPI data (1114).

Figure 12A:
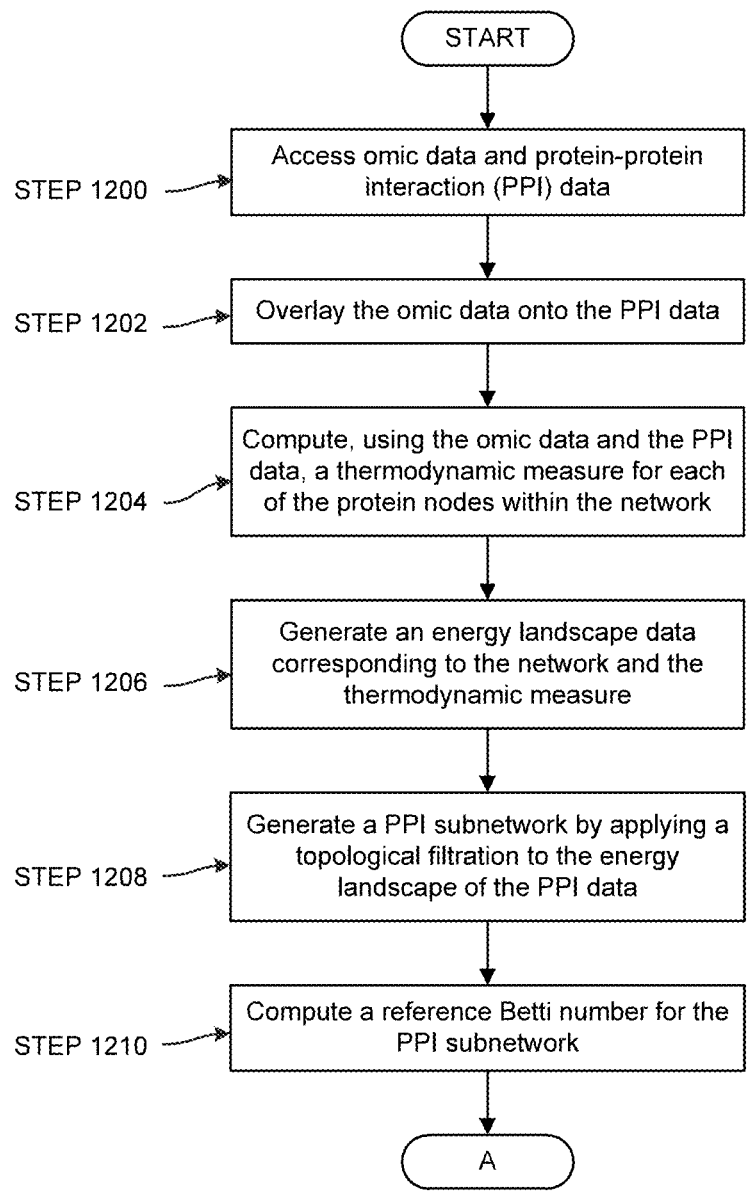
FIGS. 12A and 12B show a flowchart in accordance with one or more embodiments.
Figure 12B:
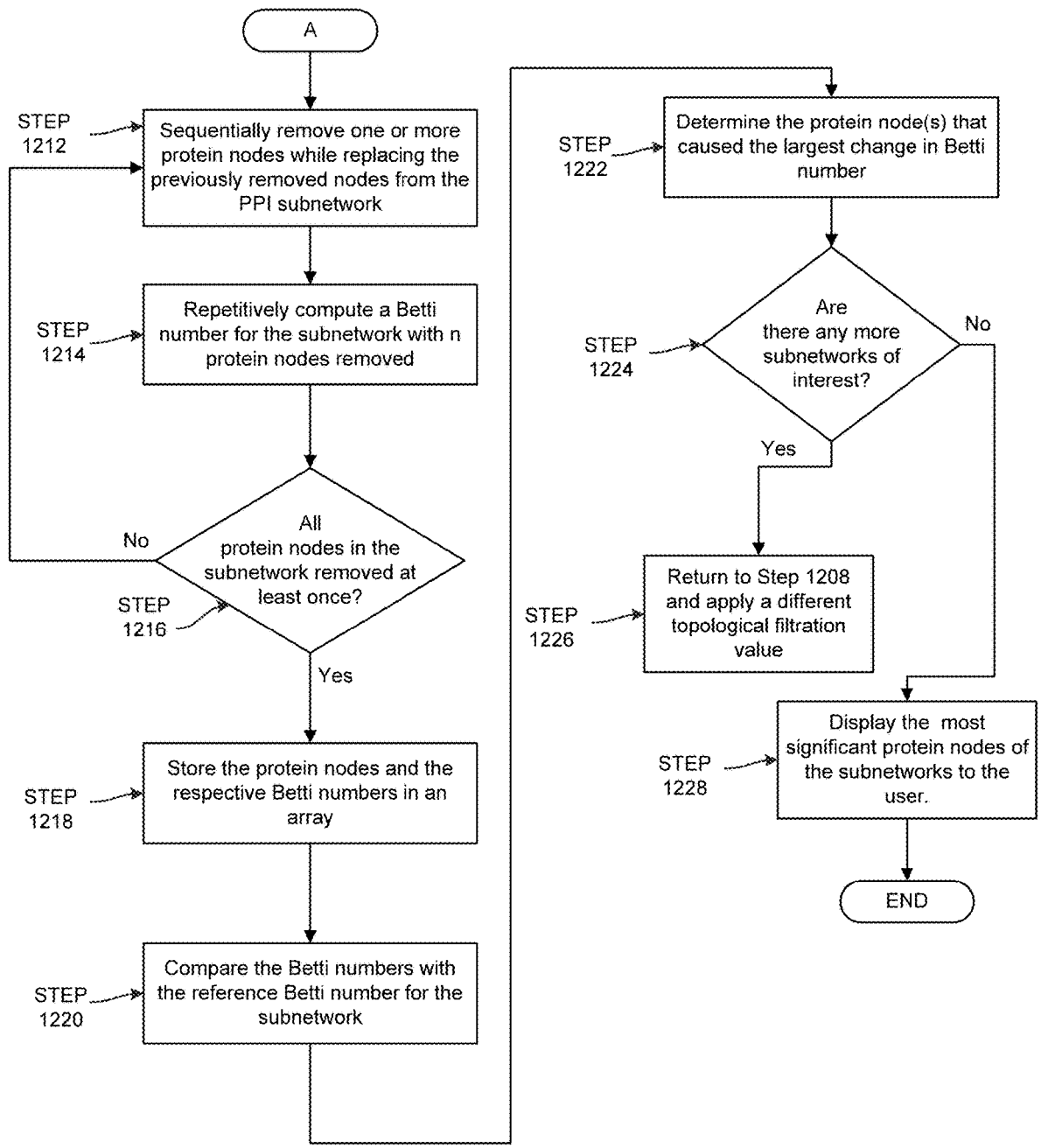

FIGS. 12A and 12B shows a flowchart of a method in accordance with one or more embodiments. In one or more embodiments, the method as shown in FIGS. 12A and 12B is a computer-implemented method. Each step shown in FIGS. 12A and 12B are described together below.

In Step 1200, the omic data and PPI data are accessed. In one or more embodiments, the omic data is the genomic information that is the RNA (e.g., mRNA, rRNA, tRNA, and other non-coding RNA) transcriptome value. In one or more embodiments, the PPI data is a PPI network, such as, but is not limited to, a human PPI network data comprising a network of protein nodes.

In one or more embodiments, the omic data and the PPI data can be obtained from at least one source including an academic database, a public database, and a private database. In one or more embodiments, the omic data and the PPI data can be stored in a data repository.

In Step 1202, the omic data is overlaid onto the PPI data. In one or more embodiments each protein node within network of the PPI data is assigned its respective omic data. Once the omic data has been overlaid, the log(2) transformed transcription data is first rescaled to be in the range [0,1]. In one or more embodiments, the most highly, positively expressed value will be set to 1.0 and the most negatively, down-regulated value will be set to 0.

It would be apparent to one of ordinary skill in the art that this is comparable to stating that the most strongly up-regulated gene produces a protein of very great concentration, relative to the most strongly down-regulated gene that will result in the lowest protein concentration.

In Step 1204, a thermodynamic measure for each of the protein nodes within the network of the PPI data is computed using the omic data. In one or more embodiments, the thermodynamic measure of each protein node is the Gibbs free energy. The Gibbs free energy is computed for each protein node by applying the rescaled value of each protein node into Equation [1]. In one or more embodiments, the overall Gibbs free energy of the PPI data can be obtained using Equation [2].

In Step 1206, an energy landscape data corresponding to the network and the thermodynamic measure is generated. In Step 1028, a PPI subnetwork is generated by applying a topological filtration to the energy landscape of the PPI data.

In one or more embodiments, the energy landscape contains a plurality of energy wells that are subnetworks of the PPI data. These PPI subnetworks are known as persistent homology. In one or more embodiments, the plurality of energy wells are also referred to as energetic subnetworks or Gibbs homology networks.

In one or more embodiments, the topological filtration is also referred to as a filtration threshold. The filtration threshold can be moved up from far below the lowest minima on an energy landscape. As the filtration threshold is moved up further, small connected PPI subnetworks, and later larger connected PPI subnetworks are revealed. In one or more embodiments, the filtration threshold can be a value in a range of approximately 5 to 7000.

It would be apparent to one of ordinary skill in the art that when the filtration threshold value is low, the complexity of the PPI subnetwork is also low. Similarly, when the filtration threshold value is high, the complexity of the PPI subnetwork is also high.

In Step 1210, a Betti number is computed for the generated PPI subnetwork. In one or more embodiments, the Betti number of the PPI subnetwork is computed based on the number of rings of four or more proteins nodes within the PPI subnetwork. This Betti number is used as a reference Betti number.

It would be apparent to one of ordinary skill in the art that as the PPI subnetwork gets more complex, the Betti number of the PPI subnetwork would also change. For example, a PPI subnetwork generated using a filtration threshold value of 10 may have a different Betti number compared to a PPI subnetwork generated using a filtration threshold value of 1000.

In Step 1212, one or more protein nodes are sequentially removed from the PPI subnetwork. In one or more embodiments, when one or more protein nodes are removed, the previously removed node(s) are replaced. In one or more embodiments, the term "sequentially" is defined as following in a sequence. For example, the protein nodes in the PPI subnetwork are removed in a predetermined sequence. This ensures that all of the protein nodes in the PPI subnetwork are removed at least once.

In Step 1214, a Betti number for the PPI subnetwork is repetitively computed each time one or more protein nodes are removed.

In Step 1216, a check is conducted to determine whether all of the protein nodes within the PPI subnetwork have been removed at least once. If the result of the check is NO, then Steps 1212 and Steps 1214 are repeated until all of the protein nodes in the PPI subnetwork have been removed at least once. If the result of the check is YES, then the protein nodes and the respective Betti numbers are stored into an array in Step 1218.

In one or more embodiments, the array in Step 1218 maps each of the removed protein node(s) to the respective Betti number computed for the PPI subnetwork with the protein node(s) removed.

In Step 1220, the recorded Betti numbers are compared to the reference Betti number computed in Step 1210.

Based on the results of Step 1220, the protein node(s) that caused the largest change in the Betti number is determined in Step 1222. In one or more embodiments, the change in the Betti number represents an effect that the protein node(s) has on a network complexity of the PPI data and the removed protein node(s) that causes a highest drop of the network complexity is the most significant protein target(s).

In one or more embodiments, the phrase "the most significant protein target(s)" is defined as the protein node(s) in a network or subnetwork that causes the largest change in Betti number when removed. In other words the "most significant" protein target(s) is the number one protein target(s) of choice when administering drugs during therapy.

In Step 1224, a determination is made whether there are other PPI subnetworks of interest. If the determination in Step 1224 results in a YES, the system returns to Step 1208 and applies a different filtration threshold value to the PPI data to obtain a different PPI subnetwork. Step 1210 to Step 1224 is then repeated for the new PPI subnetwork. If the determination in Step 1224 results in a NO, the system proceeds to Step 1228 and displays the most significant protein node(s) of the PPI subnetwork(s) to the user.

In one or more embodiments, when the complexity of the PPI subnetwork is low, removing any individual protein will drop the Betti number by the same amount resulting in as many as eight or more equivalent targets. In contrast, at high complexities, there is typically only one node that leads to the biggest drop in Betti number. In one or more embodiments the filtration threshold is optimized by identifying the best targets through a systematic application of thresholds between 8 and 128. For each threshold, the total Gibbs energy and the reference Betti number for each PPI subnetwork is computed. In one or more embodiments, the best threshold is determined as 32.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A computer-implemented method to select a protein target for therapeutic application, comprising:
   accessing genomic information and protein-protein interaction (PPI) data, the PPI data comprising a network of protein nodes from at least one source, the genomic information comprising RNA transcription data;
   computing, using the genomic information and the PPI data, a thermodynamic measure for each protein node within the network of protein nodes,
   wherein the thermodynamic measure is Gibbs free energy for each of the protein nodes within the PPI data,
   wherein said computing comprises:
   log(2) transforming and rescaling the transcription data to be in a range [0,1], computing the Gibbs free energy for each of the protein nodes within the PPI data using the rescaled transcription data and an equation of:

$$G_i = c_i \ln \frac{c_i}{\sum_{j=i} c_j}$$

wherein
   $c_i$ represents a concentration for each one of the protein nodes based on the rescaled transcription data, and $$\sum_{j=1} c_j$$

is a summation taken over concentrations $c_j$ for all neighbors to each one of the protein nodes based on the rescaled transcription data;
   generating an energy landscape data corresponding to the network of protein nodes and the Gibbs free energy for each of the protein nodes within the PPI data;
   generating a PPI subnetwork by applying a topological filtration to the energy landscape data of the PPI data,
   wherein the energy landscape data comprises a plurality of energy wells that are subnetworks of the PPI data representing persistent homology, and
   wherein the topological filtration is based on a user set filtration threshold that can be moved up from below the lowest minima in the energy landscape data to generate the PPI subnetwork, wherein an increase in the filtration threshold results in an increase in complexity of the PPI subnetwork,
   computing a first Betti number for the PPI subnetwork;
   sequentially removing a first protein node from the PPI subnetwork;
   computing a second Betti number for the PPI subnetwork with the first protein node removed;
   computing a change between the first Betti number and the second Betti number;
   replacing the first protein node into the PPI subnetwork;
   sequentially removing a second protein node from the PPI subnetwork, wherein the second protein node is different from the first protein node;
   computing a third Betti number for the PPI subnetwork with the second protein node removed and the first protein node replaced;
   computing a change between the first Betti number and the third Betti number; and
   determining, based on the change between the first Betti number and the second Betti number and the change between the first Betti number and the third Betti number, a most significant protein target within the PPI subnetwork,
wherein a change in the Betti number represents an effect that a single protein node has on a network complexity of the PPI data and a single removed protein node that causes a highest drop of the Betti number is the most significant protein target.

2. The method of claim 1, further comprising:
displaying the most significant protein target to a user.

3. The method of claim 1, further comprising:
storing, in a data repository, the genomic information and the PPI data.

4. The method of claim 3, wherein the at least one source is at least one selected from a group consisting of an academic database, a public database, and a private database.

5. The method of claim 3, wherein the genomic information is at least one transcription data selected from a group consisting of messenger RNA (mRNA), RNA sequencing (RNA-seq), and Clustered regularly interspaced short palindromic repeats (CRISPR).

6. The method of claim 1, wherein $$G_i = c_i \cdot \ln \frac{c_i}{\sum_{j=i} c_j}$$

an overall Gibbs free energy of all of the protein nodes within the PPI data is computed using an equation of:

$$qG = \sum_i G_i.$$

7. The method of claim 1, wherein the Betti number of the PPI subnetwork is a measure of the number of rings of four or more protein nodes within the PPI subnetwork.

8. The method of claim 1, wherein the Betti numbers and respective removed protein nodes are stored in an array.

9. A computing system that selects a protein target for therapeutic application, comprising:
a computer readable storage medium comprising instructions to:
access genomic information and protein-protein interaction (PPI) data comprising a network of protein nodes from at least one source, the genomic information comprising RNA transcription data;
compute, using the genomic information and the PPI data, a thermodynamic measure for each of the protein nodes within the network,
wherein the thermodynamic measure is Gibbs free energy for each of the protein nodes within the PPI data,
wherein said Gibbs free energy for each of the protein nodes is computed by:
log(2) transforming and resealing the transcription data to be in a range [0,1],
computing the Gibbs free energy for each of the protein nodes within the PPI data using the resealed transcription data and an equation of:

$$G_i = c_i \cdot \ln \frac{c_i}{\sum_{j=i} c_j}$$

wherein
$c_i$ represents a concentration for each one of the protein nodes based on the resealed transcription data, and $$\sum_{j=1} c_i$$

is a summation taken over concentrations cj for all neighbors to each one of the protein nodes based on the resealed transcription data;
generate an energy landscape data corresponding to the network and the Gibbs free energy for each of the protein nodes within the PPI data;
generate a PPI subnetwork by applying a topological filtration to the energy landscape of the PPI data,
wherein the energy landscape data comprises a plurality of energy wells that are subnetworks of the PPI data representing persistent homology, and
wherein the topological filtration is based on a user set filtration threshold that can be moved up from below the lowest minima in the energy landscape data to generate the PPI subnetwork, wherein an increase in the filtration threshold results in an increase in complexity of the PPI subnetwork;
compute a first Betti number for the PPI subnetwork;
sequentially remove a first protein node from the PPI subnetwork;
compute a second Betti number for the PPI subnetwork with the first protein node removed;
compute a change between the first Betti number and the second Betti number;
replace the first protein node into the PPI subnetwork;
sequentially remove a second protein node different from the first protein node from the PPI subnetwork;
compute a third Betti number for the PPI subnetwork with the second protein node removed and first protein node replaced;
compute a change between the first Betti number and the third Betti number; and
determine, based on the change between the first Betti number and the second Betti number and the change between the first Betti number and the third Betti number, a most significant protein target within the PPI subnetwork,
wherein a change in the Betti number represents an effect that a single protein node has on a network complexity of the PPI data and a single removed protein node that causes a highest drop of the Betti number is the most significant protein target;
processing circuitry configured to execute the instructions; and
a display circuitry configured to execute instructions to display the most significant protein target to a user.

10. The system of claim 9, further comprising:
a data repository configured to store the genomic information and the PPI data.

11. A non-transitory computer-readable medium having instructions stored thereon that, in response to execution by a computer system, cause the computer system to perform operations comprising:
accessing genomic information and protein-protein interaction (PPI) data, the PPI data comprising a network of protein nodes from at least one source, the genomic information comprising RNA transcription data;

computing, using the genomic information and the PPI data, a thermodynamic measure for each of the protein nodes within the network,
wherein the thermodynamic measure is Gibbs free energy for each of the protein nodes within the PPI data,
wherein said computing comprises:
log(2) transforming and rescaling the transcription data to be in a range [0,1], computing the Gibbs free energy for each of the protein nodes within the PPI data using the rescaled transcription data and an equation of:

$$G_i = c_i \cdot \ln \frac{c_i}{\sum_{j=i} c_j}$$

wherein
$c_i$ represents a concentration for each one of the protein nodes based on the rescaled transcription data, and $$\sum_{j=1} c_i$$

is a summation taken over concentrations $c_j$ for all neighbors to each one of the protein nodes based on the resealed transcription data;
generating an energy landscape data corresponding to the network and the Gibbs free energy for each of the protein nodes within the PPI data;
generating a PPI subnetwork by applying a topological filtration to the energy landscape of the PPI data,
wherein the energy landscape data comprises a plurality of energy wells that are subnetworks of the PPI data representing persistent homology, and
wherein the topological filtration is based on a user set filtration threshold that can be moved up from below the lowest minima in the energy landscape data to generate the PPI subnetwork, wherein an increase in the filtration threshold results in an increase in complexity of the PPI subnetwork;
computing a first Betti number for the PPI subnetwork;
sequentially removing a first protein node from the PPI subnetwork;
computing a second Betti number for the PPI subnetwork with the first protein node removed;
computing a change between the first Betti number and the second Betti number;
replacing the first protein node into the PPI subnetwork;
sequentially removing a second protein node different from the first protein node from the PPI subnetwork;
computing a third Betti number for the PPI subnetwork with the second protein node removed and first protein node replaced;
computing a change between the first Betti number and the third Betti number; and
determining, based on the change between the first Betti number and the second Betti number and the change between the first Betti number and the third Betti number, a most significant protein target within the PPI subnetwork,
wherein a change in the Betti number represents an effect that a single protein node has on a network complexity of the PPI data and a single removed protein node that causes a highest drop of the Betti number is the most significant protein target.

12. The non-transitory computer-readable medium of claim 11, wherein instructions stored thereon that, in response to execution by the computer system, cause the computer system to perform operations further comprising displaying the most significant protein target to a user.

\* \* \* \* \*